(12) United States Patent
Yang et al.

(10) Patent No.: US 11,666,263 B2
(45) Date of Patent: Jun. 6, 2023

(54) THREE DIMENSIONAL PRINTED MOLD FOR ELECTROCHEMICAL SENSOR FABRICATION, METHOD AND RELATED SYSTEM AND DEVICES THEREOF

(71) Applicant: University of Virginia Patent Foundation, Charlottesville, VA (US)

(72) Inventors: Cheng Yang, Charlottesville, VA (US); B. Jill Venton, Charlottesville, VA (US); Elefterios Trikantzopoulos, Richmond, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 994 days.

(21) Appl. No.: 16/314,492

(22) PCT Filed: Aug. 16, 2017

(86) PCT No.: PCT/US2017/047168
§ 371 (c)(1),
(2) Date: Dec. 31, 2018

(87) PCT Pub. No.: WO2018/035238
PCT Pub. Date: Feb. 22, 2018

(65) Prior Publication Data
US 2019/0246923 A1    Aug. 15, 2019

Related U.S. Application Data

(60) Provisional application No. 62/375,722, filed on Aug. 16, 2016.

(51) Int. Cl.
*A61B 5/291* (2021.01)
*A61B 5/283* (2021.01)
(Continued)

(52) U.S. Cl.
CPC ............... *A61B 5/283* (2021.01); *A61B 5/24* (2021.01); *A61B 5/291* (2021.01); *H01B 1/24* (2013.01);
(Continued)

(58) Field of Classification Search
CPC ..... A61B 2562/125; A61B 5/291; A61B 5/24; A61B 5/1459; A61B 5/1464; A61B 5/25; A61B 5/262; A61B 5/293; A61B 5/296
See application file for complete search history.

(56) References Cited

U.S. PATENT DOCUMENTS

| 4,452,249 A * | 6/1984 | Sachs | A61N 1/044 |
| | | | 427/125 |
| 2006/0135862 A1* | 6/2006 | Tootle | A61B 5/291 |
| | | | 600/373 |

(Continued)

OTHER PUBLICATIONS

Ambrosi et al., "Helical 3D-Printed Metal Electrodes as Custom-Shaped 3D Platform for Electrochemical Devices," Adv. Functional Materials, vol. 26, pp. 698-703 (2016).
(Continued)

*Primary Examiner* — Eun Hwa Kim
(74) *Attorney, Agent, or Firm* — Jenkins, Wilson, Taylor & Hunt, P.A.

(57) ABSTRACT

A method for preparing microsensors (e.g., microelectrodes) suitable for use in electrophysiology and electrochemistry studies in vitro and in vivo is described. The method can involve preparing a polymeric resin-insulated electron conducting fiber using a 3D printed mold comprising one or more channels, wherein each of the channels includes a tapered section. An electron conducting fiber partially enclosed within a metal or glass support can be laid in a channel; and a polymeric resin can be poured into the channel and cured, providing a polymer-insulated electron conducting fiber having a tapered section in proximity to a (Continued)

polymer-free electroactive tip area. For example, the method can be used to provide a polyimide-insulated carbon fiber microsensor. The mold can be used for the batch fabrication of the microsensors. The microsensors themselves, the molds for making the microsensors, and methods of using the microsensors are also described.

64 Claims, 12 Drawing Sheets

(51) Int. Cl.
  H01B 3/30 (2006.01)
  H01B 1/24 (2006.01)
  A61B 5/24 (2021.01)
  H01B 1/02 (2006.01)
  H01B 1/04 (2006.01)
  H01B 5/14 (2006.01)
(52) U.S. Cl.
  CPC ............ H01B 3/306 (2013.01); H01B 3/307 (2013.01); A61B 2562/028 (2013.01); A61B 2562/125 (2013.01); H01B 1/02 (2013.01); H01B 1/04 (2013.01); H01B 5/14 (2013.01)

(56) References Cited

U.S. PATENT DOCUMENTS

| | | | |
|---|---|---|---|
| 2010/0230132 A1 | 9/2010 | Swift et al. | |
| 2013/0211485 A1* | 8/2013 | Govindarajan | A61B 5/24 156/60 |
| 2013/0324820 A1* | 12/2013 | Petillo | C25D 7/00 205/109 |
| 2015/0250421 A1 | 9/2015 | Arumugam et al. | |
| 2016/0220135 A1* | 8/2016 | Negi | A61B 5/389 |
| 2018/0092575 A1* | 4/2018 | Bennet | A61N 1/0534 |

OTHER PUBLICATIONS

Baik"Dopamine signaling in reward-related behaviors," Front. Neural Circuits, vol. 7, No. 152, pp. 1-16 (2013).
Bath et al., "Dopamine Adsorption at Surface Modified Carbon-Fiber Electrodes," Langmuir, vol. 17, pp. 7032-7039 (2001).
Baur et al., "Fast-Scan Voltammetry of Biogenic Amines," Anal. Chem., vol. 60, No. 13, pp. 1268-1272 (1988).
Cahill et al., "Microelectrodes for the Measurement of Catecholamines in Biological Systems," Anal Chem., vol. 68, No. 18, pp. 3180-3186 (1996).
Earl et al., "Pharmacological characterisation of dopamine overflow in the striatum of the normal and MPTP-treated common marmoset, studied in vivo using fast cyclic voltammetry, nomifensine and sulpiride," J. Neurosci Methods, vol. 85, No. 2, pp. 201-209 (1998).
Ewing et al., "Pulse Voltammetry with Microvoltammetric Electrodes," Anal. Chem., vol. 53, pp. 1842-1847 (1981).
Gawron et al., "Fabrication and evaluation of a carbon-based dual-electrode detector for poly(dimethylsiloxane) electrophoresis chips," Electrophoresis, vol. 22, pp. 242-248 (2001).
Huffman et al., "Carbon-Fiber Microelectrodes for In Vivo Applications," Author Manuscript, pp. 1-18 (2010) [published in final edited form as: Analyst, vol. 134, No. 1, pp. 18-24 (2009)].
Jacobs et al., "High Temporal Resolution Measurements of Dopamine with Carbon Nanotube Yarn Microelectrodes," Anal. Chem., vol. 86, No. 12, pp. 5721-5727 (2014).
Keithley et al., "Higher Sensitivity Dopamine Measurements with Faster-Scan Cyclic Voltammetry," Anal. Chem., vol. 83, pp. 3563-3571 (2011).
Lago et al., "Assessment of Biocompatibility of Chronically Implanted Polyimide and Platinum Intrafascicular Electrodes," IEEE Trans. Biom. Eng., vol. 54, No. 2, pp. 281-290 (2007).
Li et al., "Superstructured Assembly of Nanocarbons: Fullerenes, Nanotubes, and Graphene," Chem. Rev., vol. 115, No. 15, pp. 7046-7117 (2015).
Lindsay et al., "A comparative study of thin film insulation techniques for gold electrodes," Electrochimica Acta, vol. 51, pp. 6572-6579 (2006).
Lücking et al., "3D-printed individual labware in biosciences by rapid prototyping: A proof of principle," Eng. Life Sci., vol. 15, pp. 51-56 (2015).
Maier "Low dielectric constant polymers for microelectronics," Prog. Pol. Sci., vol. 26, pp. 3-65 (2001).
Navarro et al., "A critical review of interfaces with the peripheral nervous system for the control of neuroprostheses and hybrid bionic systems," J. Periph. Nerv. Syst., vol. 10, pp. 229-258 (2005).
Ragones et al., "Disposable electrochemical sensor prepared using 3D printing for cell and tissue diagnostics," Sensors and Actuators B: Chem., vol. 216, pp. 434-442 (2015).
Rousche et al., "Flexible Polyimide-Based Intracortical Electrode Arrays with Bioactive Capability," IEEE Trans. Biom. Eng., vol. 48, No. 3, pp. 361-371 (2001).
Sandron et al., "3D Printed Metal Columns for Capillary Liquid Chromatography," Analyst, vol. 139, No. 24, pp. 6343-6347 (2014).
Sokolov et al., "Study of the Technological Limitations of Photolithography for the Relief Surface of a SOI Wafer during Formation of the Three-Dimensional Micromechanical Structure of an Integral Tensoconverter," J. Surface Inv., vol. 7, No. 1, pp. 178-180 (2013).
Sun et al, "Fabrication of Nanometer-Sized Electrodes and Tips for Scanning Electrochemical Microscopy," Anal. Chem., vol. 73, pp. 5346-5351 (2001).
Symes et al., "Integrated 3D-printed reactionware for chemical synthesis and analysis," Nature Chemistry, vol. 4, pp. 349-354 (2012).
Zachek et al. "Simultaneous monitoring of dopamine concentration at spatially different brain locations in vivo," Biosens. Bioelectron., vol. 25, pp. 1179-1185 (2010).
Chia et al, "Recent advances in 3D printing of biomaterials," J. Bio. Eng., vol. 9:4, DOI: 10.1186/s13036-015-0001-4 (2015) (14 pages).
Clark et al.,"Chronic microsensors for longitudinal, subsecond dopamine detection in behaving animals," Nat. Methods, vol. 7, pp. 126-129 (2010).
Heien et al., "Real-time measurement of dopamine fluctuations after cocaine in the brain of behaving rats," PNAS, vol. 102, pp. 10023-10028 (2005).
Kishida et al., "Sub-Second Dopamine Detection in Human Striatum," PLoS One, vol. 6, e23291 (2011) (5 pages).
Notification Concerning Transmittal of International Preliminary Report on Patentability for International Patent Application Serial No. PCT/US2017/047168 (dated Feb. 28, 2019).
Notification of Transmittal of the International Search Report and the Written Opinion of the International Searching Authority, or the Declaration for International Patent Application Serial No. PCT/US17/47168 (dated Dec. 11, 2017).
Ramsson et al., "Characterization of Fast-Scan Cyclic Voltammetric Electrodes Using Paraffin as an Effective Sealant with In Vitro and In Vivo Applications," PLoS One, vol. 10, e0141340 (2015) (15 pages).
Rengier et al., "3D printing based on imaging data: Review of medical applications," J. Cars, vol. 5, pp. 335-341 (2010) (7 pages).
Robinson et al., "Detecting Subsecond Dopamine Release with Fast-Scan Cyclic Voltammetry in Vivo," Clin. Chem., vol. 10, pp. 1763-1773 (2003).
Trikantzopoulos et al., "Novel carbon-fiber microelectrode batch fabrication using a 3D-printed mold and polyimide resin," Analyst, vol. 141, pp. 1-5 (2016).
Yang, "Development of Electrochemical Microsensors for in vivo Neurotransmitter Detection," Ph.D. Dissertation, University of Virginia, Nov. 2016 (219 pages).
Zestos et al., "Insulated Carbon Fiber and Carbon Nanotube Fiber Microelectrodes," Sensors Actuators B Chem., vol. 182, pp. 652-658 (2013).

* cited by examiner

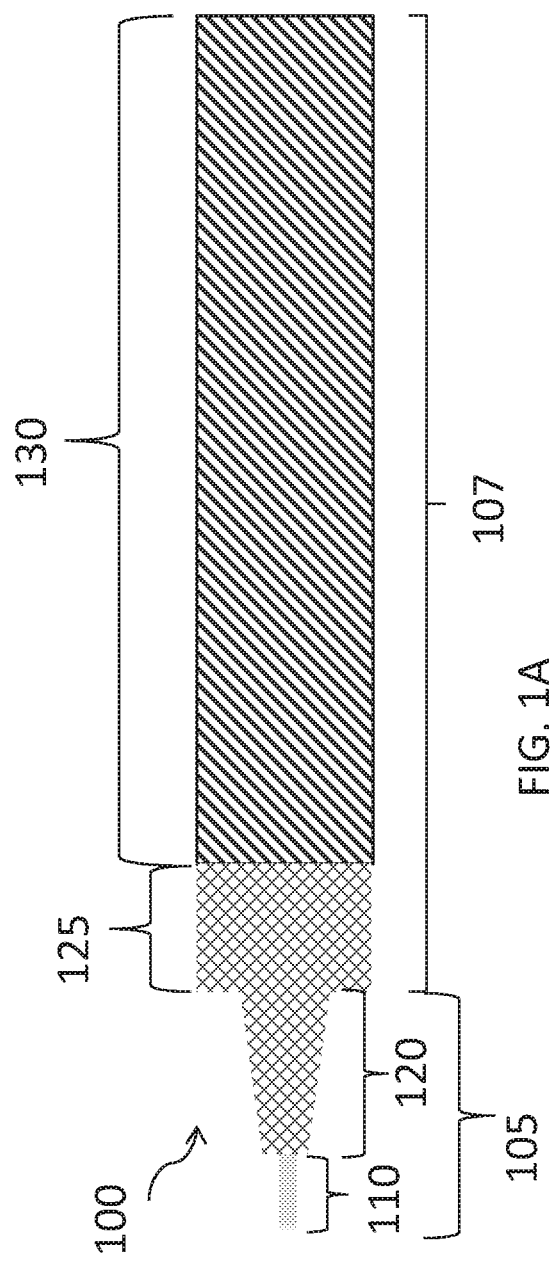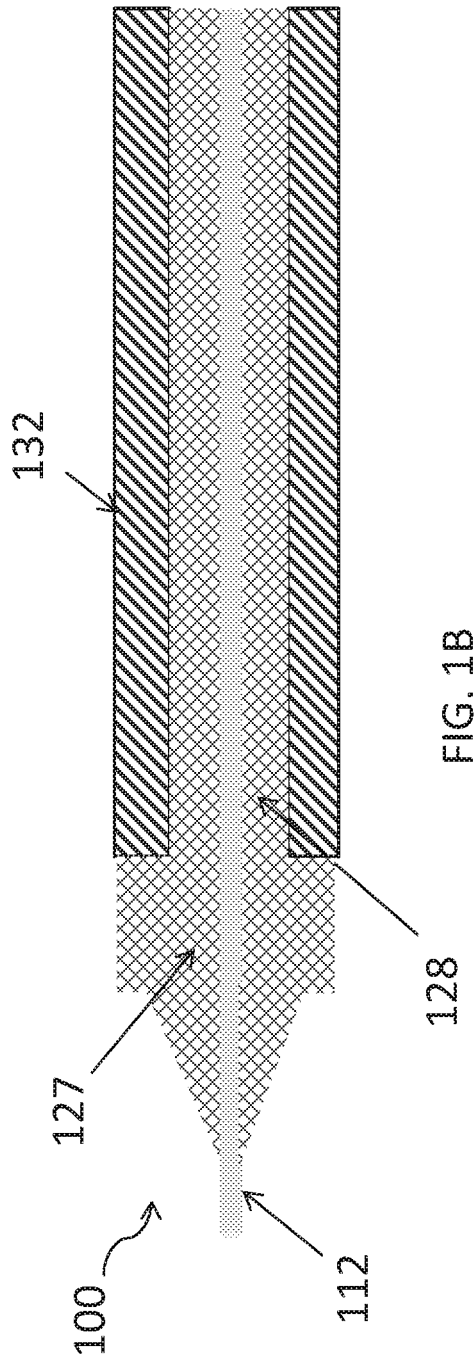

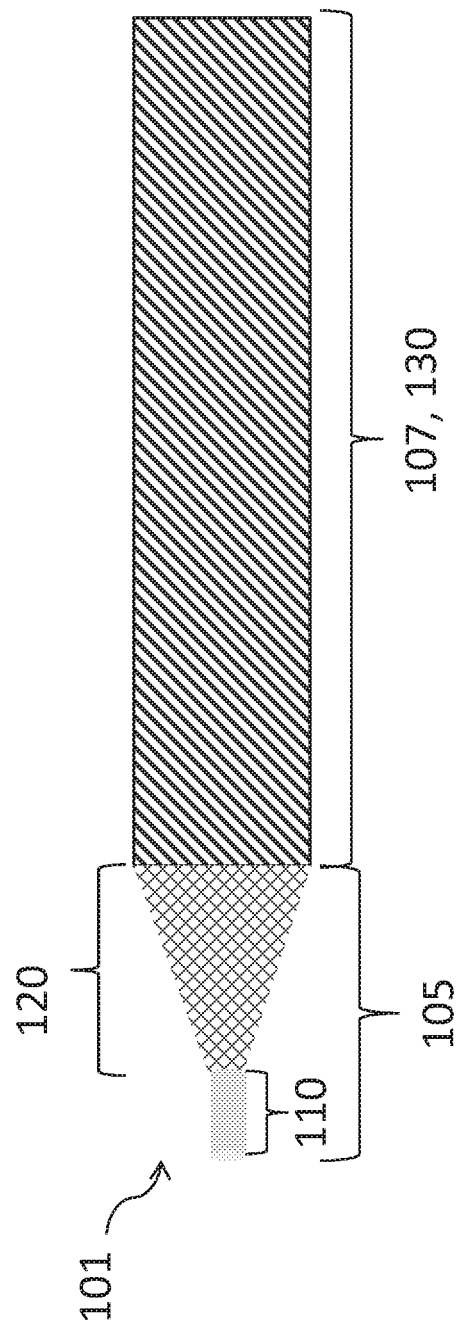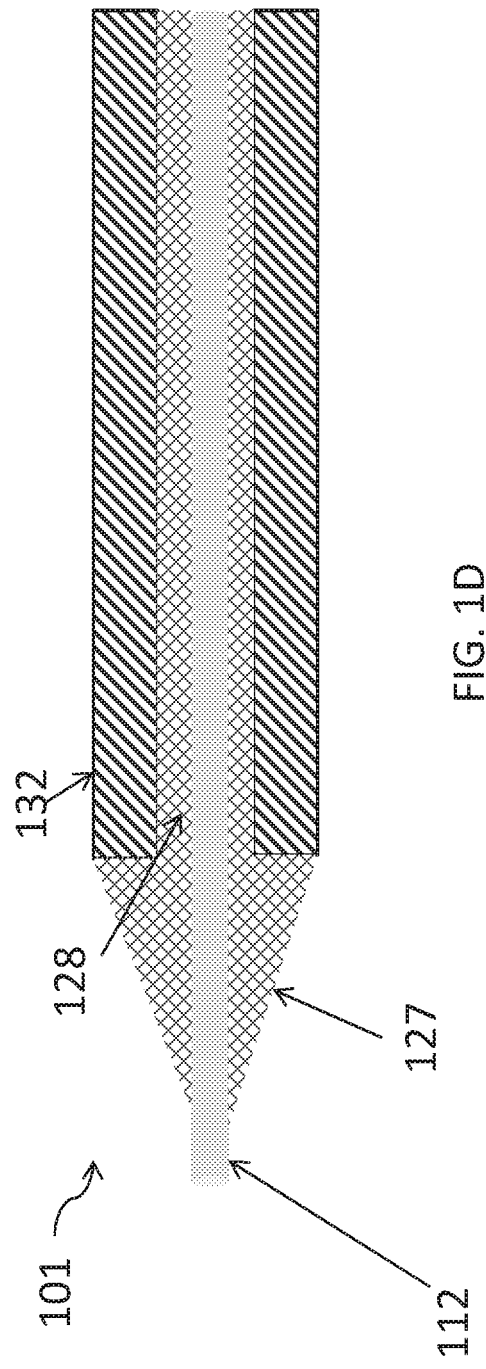

THREE DIMENSIONAL PRINTED MOLD FOR ELECTROCHEMICAL SENSOR FABRICATION, METHOD AND RELATED SYSTEM AND DEVICES THEREOF

RELATED APPLICATIONS

This application is a national phase application of PCT International Patent Application PCT/US2017/047168, filed Aug. 16, 2017, which claims the benefit of U.S. Provisional Patent Application Ser. No. 62/375,722, filed Aug. 16, 2016; each of which is incorporated herein by reference in its entirety.

STATEMENT OF GOVERNMENT SUPPORT

This invention was made with government support under Grant Nos. DA037584 and NS076875, awarded by the National Institutes of Health. The government has certain rights to this invention.

TECHNICAL FIELD

The presently disclosed subject matter relates to methods of producing microsensors and to microsensors produced by the methods. More particularly, the presently disclosed subject matter relates to methods of producing microsensors using a mold prepared via a three-dimensional (3D) printing method and to microsensors produced by the methods.

ABBREVIATIONS

Å=angstrom
° C.=degrees Celsius
%=percentage
μA=microampere
μm=micrometer (or micron)
ABS=acrylonitrile butadiene styrene terpolymer
Ag=silver
AgCl=silver chloride
CAD=computer aided design
CFME=carbon fiber microelectrode
CV=cyclic voltammogram
FSCV=fast-scan cyclic voltammogram
i.p.=intraperitoneally
kg=kilogram
mg=milligram
mm=millimeter
nA=nanoampere
nM=nanomolar
PBS=phosphate buffered saline
V=volts

BACKGROUND

Electroactive sensors have been used in numerous electrophysiology and biologically related electrochemistry applications. For instance, carbon fiber microelectrodes (CFMEs) are currently a standard tool in the detection of electroactive neurotransmitters in vivo. See Huffman and Venton, 2009. CFMEs have several properties that make them useful as in vivo probes for neurotransmitters, including biocompatibility, fast electron transfer kinetics for neurotransmitters, and good adsorption properties for biogenic amines. See Keithley et al., 2011; and Ewing et al., 1981. The traditional method for producing CFMEs involves threading a cylindrical carbon fiber into a borosilicate glass capillary that is drawn to a sharp time using a vertical capillary puller. See Cahill et al., 1996. However, this glass insulation method for CFMEs has disadvantages. See Zestos et al., 2013; and Ramsson et al., 2015. More particularly, the method involves making each CFME one at a time and includes a series of non-automated steps, thereby making mass production difficult. In addition, glass electrodes have the potential to shatter in tissue. Thus, they are not permitted for use in higher order mammals. See Kishida et al., 2011.

Accordingly, there is an ongoing need for additional methods of preparing microelectrodes, such as CFMEs, and other microsensors. In particular, there is an ongoing need for a method of preparing CFMEs and other microsensors that can be used for mass production of these items, e.g., in batches, with high reproducibility and low cost. There is also an ongoing need for additional methods that can be used in combination with a greater variety of electron conducting fibers and/or insulating materials and/or that can be easily customized for particular applications.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

Disclosed herein in some embodiments is a microsensor comprising an elongated body, wherein said elongated body comprises a first end, a second end, and a core comprising an electron conducting fiber; further wherein the elongated body comprises a first length and optionally a second length, wherein the first length comprises a tapered section and a tip end; wherein the tapered section comprises a polymer coating comprising an electronically insulating polymer material that covers the outer surface of the electron conducting fiber, further wherein a first end of the tapered section is directly adjacent to the tip end and a second end of the tapered section is at the second end of the elongated body or is directly adjacent to the second length of the elongated body and wherein the thickness of the polymer coating is thicker at the second end of the tapered section than at the first end of the tapered section, thereby providing a tapered coating layer; and wherein the tip end comprises a terminal end of the fiber that is free of a coating layer, and optionally a coated section wherein the electronically insulating polymer material covers the outer surface of the fiber.

In some embodiments, the electron conducting fiber comprises a carbon fiber, a carbon nanotube fiber, a carbon nanotube yarn, a carbon nanotube grown metal microwire, a carbon nanospikes grown metal microwire, or a metal fiber, optionally wherein said metal fiber comprises gold, platinum, tungsten, titanium, iridium, or steel. In some embodiments, the polymeric material of the polymer coating is biocompatible, optionally wherein the polymeric material comprises polyimide, further optionally wherein the polymeric coating further comprises a curing agent, a hydrogel, polyethylenimine, and/or paraffin.

In some embodiments, the tapered section has a length of about 5 millimeters (mm) or more. In some embodiments, the tip end has a length of between about 50 micrometers (μm) and about 50 millimeters (mm), optionally wherein the tip end has a length of about 50 μm to about 300 μm when there is no coated section of the tip end or wherein the tip end has a length of about 3 mm to about 50 mm when there is a coated section of the tip end, optionally wherein an uncoated portion of the tip end has a length of about 50 μm to about 300 μm.

In some embodiments, the electron conducting fiber has a diameter of between about 7 μm and about 50 μm, optionally wherein the fiber has a diameter of about 7 μm.

In some embodiments, the second length of the elongated body comprises a support section, wherein said support section comprises a support material positioned over the outer surface of the electron conducting fiber. In some embodiments, at least one length of support material is positioned over an inside polymer coating, under an outside polymer coating, or between an inside polymer coating and an outside polymer coating, wherein the inside and/or outside polymer coating comprise the same polymeric material as the polymer coating of the tapered section. In some embodiments, the support material comprises glass or metal.

In some embodiments, the polymer coating of the tapered section extends into the second length of the elongated body, and the second length further comprises a non-support section positioned between the support section and the tapered section of the first length of the elongated body, wherein the non-support section comprises the polymer coating and the electron conducting fiber and optionally wherein the thickness of the polymer coating is approximately the same over the entire length of the non-support section. In some embodiments, the non-support section has a length of about 3 mm or longer. In some embodiments, the support section has a length of about 15 mm or longer. In some embodiments, the outer diameter of the support section is about 1.5 mm or less.

In some embodiments, the length of the elongated body is about 23 mm or longer, optionally between about 23 mm and about 200 mm. In some embodiments, the microsensor is produced using a mold prepared via a three dimensional printing method. In some embodiments, the elongated body comprises two or more electron conducting fibers, optionally wherein each electron conducting fiber has a separate first length comprising a tapered section and a tip end.

In some embodiments, the presently disclosed subject matter provides a microsensor array comprising at least two microsensors of the presently disclosed subject matter.

In some embodiments, the presently disclosed subject matter provides a mold for preparing a microsensor, wherein the mold comprises at least one channel comprising at least one channel section having a first end and a second end, wherein the channel section tapers from the first end of the channel section to the second end of the channel section such that a width of the channel section at the second end of the channel section is narrower than a width of the channel section at the first end of the channel section. In some embodiments, the at least one channel comprises at least two sections: (a) a first channel section adjacent to a side edge of the mold and having a first channel width, optionally wherein the first channel section has a length of about 15 millimeters (mm) or longer; and (b) a second channel section adjacent to the first channel section, optionally wherein the second channel section has a length of about 5 mm or longer, wherein the second channel section has channel walls that taper from a first end of the second channel section adjacent to the first channel section to a second end of the second channel section, such that the width of the first end of the second channel section is larger than the width of the second end of the second channel section.

In some embodiments, the channel comprises at least three sections: (a) a first channel section adjacent to a side edge of the mold, optionally wherein the first channel section has a length of about 15 millimeters (mm) or longer; (b) a second channel section adjacent to the first channel section, optionally wherein the second channel section has a length of about 5 mm or longer; and (c) a third channel section adjacent to the second channel section, optionally wherein the third channel section has a length of about 3 mm or longer; and wherein the first channel section has a first channel width, optionally wherein the first channel width ranges from about 200 micrometers (μm) to about 1000 μm, further optionally about 640 μm; wherein the third channel section has a third channel width that is smaller than the first channel width, optionally wherein the third channel width ranges from about 10 μm to about 200 μm, further optionally about 150 μm, and wherein the second channel section has channel walls that taper from an end of the first channel section to an end of the third channel section.

In some embodiments, the mold comprises two or more channels, optionally wherein the mold comprises at least about 40 channels. In some embodiments, the mold is produced via a three-dimensional printing process. In some embodiments, the mold comprises an acrylonitrile butadiene styrene terpolymer (ABS).

In some embodiments, the presently disclosed subject matter provides a method of producing a microsensor, wherein said method comprises: (a) providing a mold that comprises at least one channel comprising at least one channel section having a first end and a second end, wherein the channel section tapers from the first end of the channel section to the second end of the channel section such that a width of the channel section at the second end of the channel section is narrower than a width of the channel section at the first end of the channel section; (b) inserting an electron conducting fiber into a support material, optionally wherein the support material comprises a glass capillary material or a metal material; (c) placing the support material in a channel in the mold, such that the support material is present in the channel and wherein a length of the fiber is present in the channel, optionally wherein another length of the fiber is positioned outside the channel or in a channel section having a width such that when the fiber is present in the channel section the fit is secure enough to retard polymeric material from flowing into the channel section; (d) filling the channel with a polymeric material; (e) curing the polymeric material to provide a microsensor; and (f) removing the microsensor from the mold.

In some embodiments, the method comprises: (a) providing a mold of the presently disclosed subject matter that comprises a channel comprising at least three sections: a first channel section adjacent to a side edge of the mold, a second channel section adjacent to the first channel section, and a third channel section adjacent to the second channel section, wherein the third channel section has a width that is smaller than the width of the first channel and wherein the second channel section has channel walls that taper from an end of the first channel section to an end of the third channel section; (b) inserting an electron conducting fiber into a support material, optionally wherein the support material comprises a glass capillary material or a metal material; (c) placing the support material in a channel in the mold, such that the support material is present in the first channel section and wherein a length of the fiber is present the second and third section of the channel; (d) filling the channel with a polymeric material; (e) curing the polymeric material to provide a microsensor; and (f) removing the microsensor from the mold.

In some embodiments, the method further comprises trimming exposed fiber to a desired length. In some embodiments, the method further comprises sealing an end of the microsensor adjacent to the first channel section with a resin, optionally an epoxy resin.

In some embodiments, the curing is performed by heating the mold to a first temperature for a first period of time, optionally wherein the first temperature is between about 100° C. and about 150° C. and/or wherein the first period of time is between about 5 minutes and about 60 minutes, further optionally wherein the first temperature is about 150° C. and/or wherein the first period of time is about 30 minutes. In some embodiments, the method further comprises adding additional polymeric material to the channel following the curing and then curing the additional polymeric material.

In some embodiments, the method comprises preparing a plurality of microsensors by preparing a microsensor in each of a plurality of the channels of a mold simultaneously. In some embodiments, the mold is reused one or more times to make additional microsensors using one or more channels in which a microsensor has been previously prepared. In some embodiments, the presently disclosed subject matter provides a microsensor prepared according to the presently disclosed method.

In some embodiments, the presently disclosed subject matter provides a method of detecting electrical activity, wherein the method comprises providing a microsensor as described herein; contacting the microsensor to a sample, optionally a biological sample, further optionally an in vivo biological sample; and detecting an electrical signal using said microsensor. In some embodiments, the sample comprises a cell, a tissue or an organ, optionally wherein the sample comprises brain or heart tissue. In some embodiments, the microsensor is configured for use as a microelectrode, and detecting the electrical activity detects a biological molecule, optionally wherein the biological molecule is a neurotransmitter.

In some embodiments, the presently disclosed subject matter provides a method of detecting a biological molecule, wherein the method comprises providing a microsensor as described herein, wherein said microsensor is configured for use as a microelectrode; and detecting the biological molecule using the microsensor, optionally via a cyclic voltammetry technique. In some embodiments, the detecting is performed in vivo and the microsensor is present in a tissue of a living subject, optionally where the microsensor is inserted in a brain tissue of a subject. In some embodiments, the biological molecule is a neurotransmitter, optionally wherein the biological molecule is a biogenic amine, further optionally wherein the biogenic amine is dopamine.

Accordingly, it is an object of the presently disclosed subject matter to provide a microsensor comprising an electron conducting fiber core and a coating layer comprising an electronically insulating polymeric material, methods of making the microsensor, molds configured for use in preparing the microsensors, and methods of using the microsensors. This and other objects are achieved in whole or in part by the presently disclosed subject matter.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). A further understanding of the presently disclosed subject matter can be obtained by reference to an embodiment set forth in the illustrations of the accompanying drawings. Although the illustrated embodiment is merely exemplary of the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, but merely to clarify and exemplify the presently disclosed subject matter.

For a more complete understanding of the presently disclosed subject matter, reference is now made to the following drawings in which:

FIG. 1A is a schematic drawing of a top view of a microsensor according to one embodiment of the presently disclosed subject matter.

FIG. 1B is a schematic drawing of a cross-sectional side view of the microsensor of FIG. 1A.

FIG. 1C is a schematic drawing of a top view of a microsensor according to one embodiment of the presently disclosed subject matter.

FIG. 1D is a schematic drawing of a cross-sectional side view of the microsensor of FIG. 1C.

DETAILED DESCRIPTION

Figure 1E:
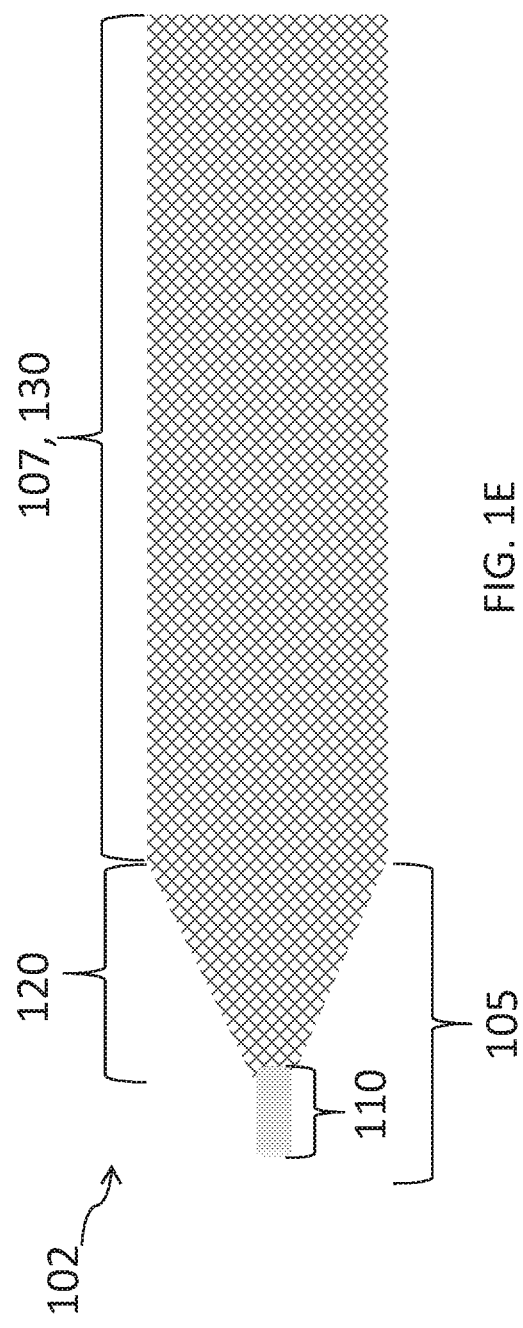
FIG. 1E is a schematic drawing of a top view of a microsensor according to one embodiment of the presently disclosed subject matter.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. Although any methods, devices, and materials similar or equivalent to those described herein can be used in the practice or testing of the presently disclosed subject matter, representative methods, devices, and materials are now described. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "an electron conducting fiber" includes a plurality of such fibers, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

Numerical ranges recited herein by endpoints include all numbers and fractions subsumed within that range (e.g. 1 to 5 includes, but is not limited to, 1, 1.5, 2, 2.75, 3, 3.90, 4, and 5).

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

The term "microsensor" as used herein refers to a sensor comprising at least one component comprising an electronically conductive material suitable for use in measuring an electrical activity and having at least one of a length, width, and/or diameter that is less than about 1 millimeter. In particular, the term "microsensor" as used herein refers to a sensor suitable for electrochemical and/or electrophysiology studies. In some embodiments, the length, width and/or diameter is less than about 500 mm, less than about 250 mm, less than about 200 mm, less than about 100 mm, or less than about 50 mm. In some embodiments, the length, width, and/or diameter is between about 100 mm and about 50 μm.

The term "biocompatible" as used herein refers to a material that is non-harmful (e.g. non toxic) to living tissues.

The term "biological molecule" as used herein can refer to molecules synthesized in and/or that produce a biological response in an animal, plant and/or microorganism (e.g., a bacteria, virus or fungi). Exemplary biological molecules include, but are not limited to, an antigen, an antibody, a hormone, an enzyme, a carbohydrate, a lectin, a peptide, a protein, a lipid, a nucleotide, an oligonucleotide, an amino acid, a drug, and a neurotransmitter.

The term "biogenic amine" refers to an amine that is the result of a biological process, e.g., metabolism, etc.

The term "neurotransmitter" refers to a molecule that is synthesized and/or present in a neuron, and that can be released from a neuron to produce a response in a target. For example, neurotransmitters can be released into the synaptic cleft and received by receptors on a target cell. Neurotransmitters include, but are not limited to, aminoacids such as glutamine, glycine, γ-aminobutyric acid (GABA), D-serine, and aspartate; histamine; serotonin; catecholamines, such as norepinephrine, epinephrine, and dopamine; phenethylamines, such as phenethylamine, N-methylphenethylamine and phenylethanolamine; thyronamines; tryptamines (e.g., melatonin); peptides, such as substance P and somatastatin; acetylcholine; and purines, such as adenosine; as well as their metabolites.

II. General Considerations

Since methods for the electrochemical detection of biomolecules are generally based on having a known amount of exposed electrochemically active surface area, electrodes typically include areas that are insulated. Microelectrodes for neurotransmitter detection are currently generally manufactured one at a time by inserting a carbon fiber microelectrode into a glass capillary and then pulling it into a fine tip. See Baur et al., 1988; and Cahill et al., 1996. However, this usual method of producing microelectrodes with glass capillaries has some drawbacks. First, during production, the electrode material is exposed to heat and force from a puller. Some possible electrode materials, such as carbon nanotube fibers, break under these conditions. See Li et al., 2015. Second, glass electrodes can potentially shatter in the tissue being assayed, making it dangerous to use such electrodes in living subjects. Accordingly, in vivo testing using a glass electrode is not permitted in higher order mammals. See Earl et al., 1998. Further, mass production of CFMEs is difficult by this method.

One alternative method of producing microelectrodes involves inserting the electrode into a polyimide-coated, fused silica capillary and epoxy sealing the end. See Jacobs et al., 2014. But, manually inserting electrode materials, such as carbon fibers and metal wires into fused silica capillaries is tedious, not amendable to mass production, and the electrode design is not customizable.

One method to mass produce small objects reproducibly is by using a mold. Making electrodes in a mold can involve the use of an insulation material other than glass, which can be beneficial for preparing electrodes that are more biocompatible and shatter resistant than glass-insulated electrodes. Poly(dimethylsiloxane) (PDMS) molds have been made extensively using photolithography. A laser-etched mold was previously reported for use in making epoxy-insulated electrodes. See Zestos et al., 2013. While this method was more amenable to mass fabrication, control of the dimensions of the mold channels could be difficult to achieve.

The recent development of three dimensional (3D) printing-based rapid protoypes has led to the consumer-oriented availability of desktop or bench-top printing devices. See Lücking et al., 2014. Generally, 3D printing technology can relate to a layered fabrication process used for the rapid production of three-dimensional objects directly from digital computer aided design (CAD). See Sandron et al., 2014. The 3D printing process allows 3D objects to be fabricated in a bottom-up, additive fashion directly from digital designs, with no milling or molding. This can provide, among other things, the cost-effective use of self-developed and individually designed labware in the area of bioscience. Compared to conventional labware produced by milling or molding, 3D printed labware has the advantage of completely customizable design, mass production, high reproducibility, and low cost.

Thus, according to one aspect of the presently disclosed subject matter, a method of producing microelectrodes and other microsensors using a mold prepared via a 3D printing method is provided. In some embodiments, the mold is used in combination with a bio-compatible insulating agent, such as a polyimide or epoxy resin. In particular, the presently disclosed subject matter is believed to describe, for the first time, a method for fabricating electrochemical probes with micron diameters and/or particular geometries (e.g., tapered sections) using 3D printed devices. To make electrodes according to the presently disclosed subject matter a 3D printed mold is prepared with one or more channels, wherein each channel has a tip width/diameter, for example, of about 200 μm or less. The size and geometry of the channels is customizable. The electrodes can be removed from the mold easily, e.g., by slightly bending the mold and removing the electrode with the aid of a tweezers. This method provides a rapid and low cost fabrication method for microsensors with high resolution features, high-biocompatibility, and can be readily employed for the mass production of the microsensors. In addition, the method is compatible with a variety of electron conducting fibers, some of which are not compatible with traditional glass capillilary pulling methods of microsensor production.

According to one exemplary embodiment, a carbon fiber is placed in the mold and then a polyimide resin is added to the channel and cured by placing the mold in an oven. The resulting polyimide-insulated CFMEs show comparable sensitivity, stability, and temperal resolution to glass-insulated CFMEs, and are suitable for in vivo electrophysiology and/or electrochemistry studies. In particular, because of the flexibility and biocompatibility provided by the polyimide, these electrodes can be used as a safer microsensor to replace glass-insulated CFMEs.

According to one aspect of the presently disclosed subject matter is provided a 3D printed mold for the fabrication of electrochemical sensors (e.g., microsensors) and related systems and devices. The mold can be digitally designed by CAD software. Accordingly, the mold and the sensors produced therefrom are completely customizable. Further, the molds can be reused several times before the detail of the mold channels begins to deteriorate. In addition, the mold is compatible with a variety of insulaters, e.g., so that the stiffness and other properties of the microsensors can be customized.

According to one aspect of the presently disclosed subject matter there is provided a microsensor produced using a 3D printed mold and related methods of use thereof, e.g., to detect electrical activity in vivo and/or to detect biological molecules, such as neurotransmitters, in vivo, e.g., in brain tissues. The microsensors can be significantly less expensive than the present commercially available microsensors and also have unique and customizable microscale dimensions and geometries, as well as customizable combinations of electron conducting and electron insulating materials.

III. Microsensors

The presently disclosed subject matter provides, in some embodiments, a microsensor comprising an elongated body, wherein the elongated body comprises a core comprising an electron conducting fiber, wherein at least a portion of the outer surface of the electron conducting fiber is coated with an electrically insulating polymer material. In some embodiments, at least a portion of the coated portion of the elongated body has a tapered shape. In some embodiments, the longitudinal axis of the electron conducting fiber is parallel to the longitudinal axis of the elongated body. In some embodiments, the electron conducting fiber and the elongated body are coaxial. The elongated body can have a square, rectangular, triangular, circular or oval cross-sectional shape. In some embodiments, the elongated body has a circular cross-section and the elongated body is generally cylindrical. In some embodiments, the elongated body has a length of about 10 millimeters (mm) or longer. In some, embodiments, the elongated body has a length of between about 10 mm and about 200 mm (e.g., 10, 15, 20, 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, or about 200 mm).

In some embodiments, the elongated body comprises a first length or a first length and a second length, wherein the first length comprises a tapered section and a tip end. In some embodiments, the tip end comprises a terminal end of the fiber that is free of a coating layer (e.g., the polymer material and/or any other materials). In some embodiments, the tapered section comprises a polymer coating comprising an electronically insulating polymer material that covers the outer surface of the electron conducting fiber. In some embodiments, the first end of the tapered section is directly adjacent to the tip end (which can reside at a first end of the elongated body) and a second end of the tapered section constitutes the second end of the elongated body or is directly adjacent to the second length of the elongated body. In some embodiments, the thickness of the polymer coating is thicker at the second end than at the first end of the tapered section, thereby providing a tapered coating layer. In some embodiments, a portion of the tip end is covered by a coating layer (e.g., the polymer material and/or any other materials) such that the tip end includes a coated section in addition to the terminal end that is free of a coating layer.

The electron conducting fiber can be of any suitable material or materials. In some embodiments, the electron conducting fiber is selected from the group including, but not limited to, a carbon fiber, a carbon nanotube fiber, a carbon nanotube yarn, a carbon nanotube grown metal microwire, a carbon nanospikes grown metal microwire, and a metal fiber. Suitable metal fibers can include fibers of metals or metal alloys selected from, but not limited to, gold (Au), platinum (Pt), tungsten (W), titanium (Ti), iridium (Ir), or steel. In some embodiments, the electron conducting fiber has a diameter of between about 7 μm and about 50 μm (e.g., about 7, 10, 12, 15, 17, 20, 22, 25, 27, 30, 32, 35, 37, 40, 42, 45, 47, or about 50 μm). In some embodiments, the electron conducting fiber is a carbon fiber and/or has a diameter of about 7 μm.

The polymeric material of the polymer coating can be any suitable electronically insulating material. In some embodiments, the polymer is a thermosetting polymer. In some embodiments, the polymer material can be selected, for example, based on its suitability for use in preparing molded objects (e.g., the flowability of its corresponding resin material and/or having convenient curing conditions) and/or its mechanical flexibility. In some embodiments, the polymer material is biocompatible. In some embodiments, the polymeric material is a polyimide or an epoxy polymer. In some embodiments, the polymeric material is a polyimide. Polyimides can be prepared by the polymerization of dianhydrides with a diamine or a diisocyanate. In some embodiments, the polymer coating comprises a curing agent, a hydrogel, polyethylenimine, and/or paraffin. These components can alter the stiffness or other properties of the sensors.

The tapered section of the presently disclosed microsensor can increase the usefulness and/or safety of the microsensor in in vivo studies, particularly in in vivo brain tissue studies, as the tapered section can decrease the size of the part of the sensor nearest the electroactive tip (i.e., the terminal end) and thus the size of the part of the sensor that is inserted in (or that is inserted to the greatest depth in) the brain tissue. Thus, less brain tissue is disturbed and/or damaged via the use of the presently disclosed microsensor. In some embodiments, the tapered section has a length of about 5 mm or more (e.g., about 5, 6, 7, 8, 9, 10, 12, 15, 18, 20, 25, 30, 35, 40, 50, 60, 70, 80, 90, or 100 mm or more). In some, embodiments, the tapered section has a length of between about 10 mm and about 200 mm (e.g., 10, 15, 20, 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, or about 200 mm). The length of the tapered section can be varied based upon the size of the tissue, organ, or organism in which the microsensor is to be used or upon the location of the tissue within the organ. Thus, if the sensor is intended for use in a larger organism (e.g., a human), the tapered section can be longer than the tapered section of a sensor intended for use in a smaller animal (e.g., a mouse or rat).

In some embodiments, the tip end has a length of between about 50 micrometers (μm) and about 50 millimeters (mm) (e.g., about 50, 75, 100, 125, 150, 175, 200, 225, 250, 275, 300, 400, 500, or 1,000 μm, or about 3, 5, 10, 15, 20, 25, 30, 35, 40, 45, and 50 mm). The tip end can be adjusted based upon the amount of electroactive surface area desired. In some embodiments, the tip end has a length of between about 50 μm and about 300 μm (e.g., about 50, 75, 100, 125, 150, 175, 200, 225, 250, 275, or 300 μm). In some embodiments, the tip end has a length of between about 100 μm and about 150 μm (e.g., 100, 105, 110, 115, 120, 125, 130, 135, 140, 145, or about 150 μm). In some embodiments, the tip end has a length that is longer than about 150 μm. In some embodiments, the tip end has a length of about 50 μm to about 300 μm when there is no coated section of the tip end. In some embodiments, the tip end has a length of about 3 mm-50 mm when there is a coated section of the tip end, optionally wherein an uncoated portion of the tip end has a length of about 50 μm to about 300 μm.

In some embodiments, the second end of the elongated body comprises a support section. In some embodiments, the support section comprises a support material positioned over the outer surface of the electron conducting fiber. The support material can comprise a glass, a silica, or a metal (e.g., stainless steel) material. For example, the support material can comprise a glass capillary or a metal cannula that is coaxial with the electron conducting fiber. The outer diameter of the capillary or cannula can be about 1.5 mm or less (e.g., about 1.5 mm, 1.4 mm, 1.3 mm, 1.2 mm, 1.1, mm, 1.0 mm, 0.9 mm, 0.8 mm, 0.7 mm, 0.6 mm, or about 0.5 mm or less).

In some embodiments, the support section has a length of about 15 mm or longer (e.g., 15 mm, 20 mm, 25 mm, 30 mm, 35 mm, 40 mm, 45 mm, 50 mm, or longer). In some embodiments, the outer diameter of the support section is about 1.5 mm or less (.e.g. about 1.5 mm, 1.4 mm, 1.3 mm, 1.2 mm, 1.1, mm, 1.0 mm, 0.9 mm, 0.8 mm, 0.7 mm, 0.6 mm, or about 0.5 mm or less).

The polymer coating of the tapered section can extend into the support section, e.g., over and/or under the support material, for at least a portion of the length of the support section. Thus, in some embodiments, at least one length of the support material is positioned over an inside polymer coating (i.e., a polymer coating between the electron conducting fiber and the support material (e.g., the inner surface of the glass capillary or metal cannula), under an outside polymer coating (i.e., a polymer coating that present on the outer surface of the elongated body (e.g., on the outside surface of the glass capillary or metal cannula), or between an inside polymer coating and an outside polymer coating. The inside and/or outside polymer coating can generally comprise the same polymeric material as the polymer coating of the tapered section. In some embodiments, the polymer coating extends into the support section for the full length of the support section.

Optionally, the second length of the elongated body can also include a non-support section, wherein the non-support section is positioned directly between the tapered section and the support section. The non-support section can comprise a length of the electron conducting fiber wherein the outer surface of the fiber is coated with the electronically insulating polymeric material. In some embodiments, the coating has an approximately uniform thickness. In some embodiments, the non-support section has a length of about 0.5 mm or longer. In some embodiments, the non-support section has a length of about 3 mm or longer (e.g., about 3 mm, 4 mm, 5 mm, 6 mm, or longer).

In some embodiments, the combined length of the first and second lengths of the elongated body can be about 23 mm or longer. In some embodiments, the combined first and second lengths is between about 23 mm and about 100 mm (e.g., about 23, 25, 30, 35, 40, 45, 50, 55, 60, 65, 70, 75, 80, 85, 90, 95, or about 100 mm). In some, embodiments, the combined first and second lengths is between about 10 mm and about 200 mm (e.g., 10, 15, 20, 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, or about 200 mm).

The second end of the second length of the elongated body (i.e., the end that is not adjacent to the first length of the elongated body) can be sealed with a suitable material (e.g. an epoxy or paraffin wax). The second end can further be connected (i.e., in electrical communication) to other sensor components (e.g., an amplifier, a potentiostat, etc.).

In some embodiments, the elongated body can comprise two or more electron conducting fibers. In some embodiments, each electron conducting fiber can have a separate first length, wherein each first length comprises a tapered section (comprising electronically insulating polymeric material and a length of fiber) and a tip end (comprising a terminal end comprising a length of uncoated fiber). In some embodiments, the elongated body comprises two electron conducting fibers, wherein one fiber can serve as a working electrode and the second fiber can serve as a reference electrode. In some embodiments, at least two or more microsensors of the presently disclosed subject matter can be combined in a single housing and/or used in combination as a microsensor array.

In some embodiments, the presently disclosed microsensor is produced using a mold prepared via a 3D printing method. Exemplary molds are described further hereinbelow. In some embodiments, the presently disclosed microsensor is batch/mass produced using a 3D printed mold. For example, the microsensors can be produced in a batch and stored, e.g., under ambient conditions, until use. The microsensors can be stored, for example, for one or more days, weeks or months prior to use.

Exemplary microsensors are now described in more detail with reference to FIGS. 1A-1H. More particularly, FIGS. 1A and 1B show a top view and a cross-sectional side view of exemplary microsensor 100 of the presently disclosed subject matter. Microsensor 100 comprises a first length 105 and a second length 107. First length 105 includes tip end 110 of electron conducting fiber 112 and tapered section 120 comprises polymer coating material 127 coating the outer surface of fiber 112 and having a tapering outer surface. Second length 107 includes support section 130 comprising a support material 132 and non-support section 125 comprising polymer coating 127 that has a non-tapering outer surface. Polymer coating 127 extends into the support section, providing inner polymer coating 128 between the surface of fiber 112 and the inner surface of support material 132.

FIGS. 1C and 1D show a top view and a cross-sectional side view of an exemplary microsensor of the presently disclosed subject matter that does not include the optional non-support section of the second length of the elongated body. Microsensor 101 comprises a first length 105 and a second length 107. First length 105 includes tip end 110 of an electron conducting fiber 112 and tapered section 120 further comprising polymer coating 127 having a tapering outer surface. Second length 107 comprises support section 130, which further includes support material 132. Polymer coating 127 extends into the support section, providing inner polymer coating 128 between the surface of fiber 112 and the inner surface of support material 132.

Figure 1F:
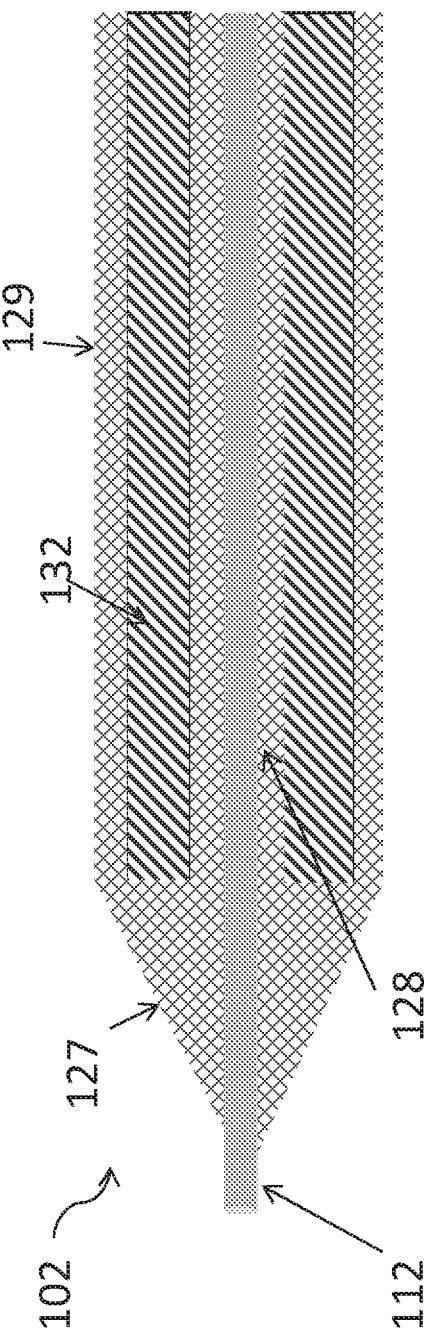
FIG. 1F is a schematic drawing of a cross-sectional side view of the microsensor of FIG. 1E.

FIGS. 1E and 1F show a top view and a cross-sectional side view of another exemplary microsensor of the presently disclosed subject matter that does not include the optional non-support section of the second length of the elongated body. Microsensor 102 comprises a first length 105 and a second length 107. First length 105 includes tip end 110 of electron conducting fiber 112 and tapered section 120 further comprising polymer coating 127 having a tapering outer surface. Second length 107 includes support section 130. Polymer coating 127 extends into support section 130, which comprises outer polymer coating 129, which is present over the outer surface of support material 132. Inner polymer coating 128 is present between the surface of fiber 112 and the inner surface of support material 132.

Figure 1G:
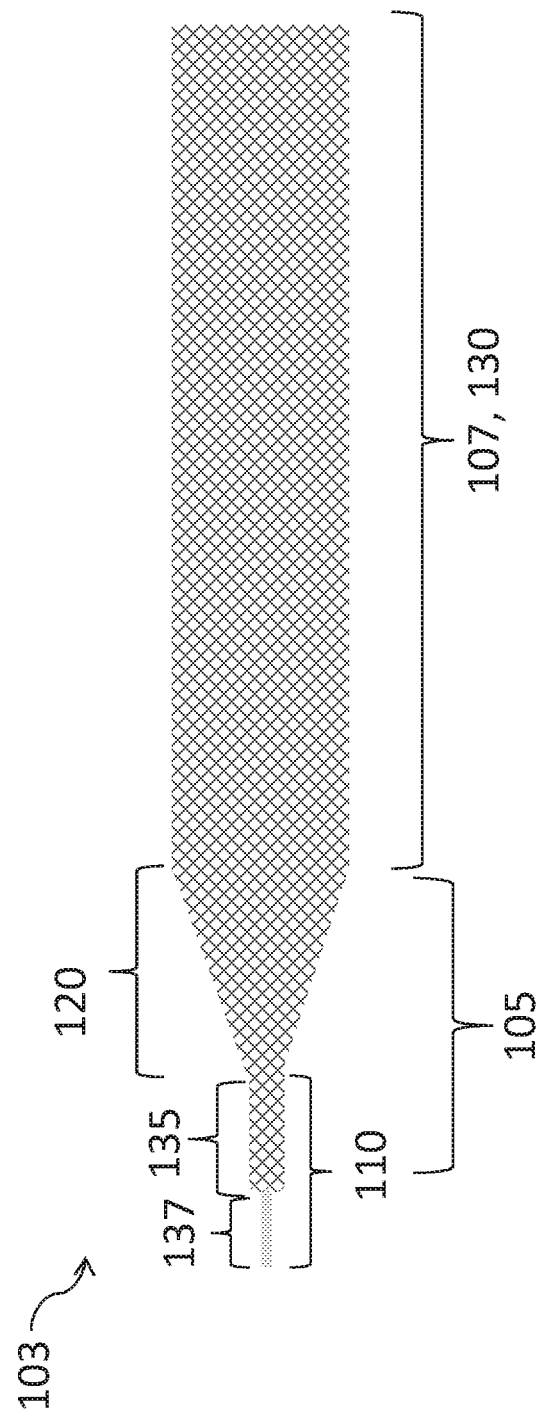
FIG. 1G is a schematic drawing of a top view of a microsensor according to one embodiment of the presently disclosed subject matter, wherein a portion of the tip end has a coating layer.
Figure 1H:
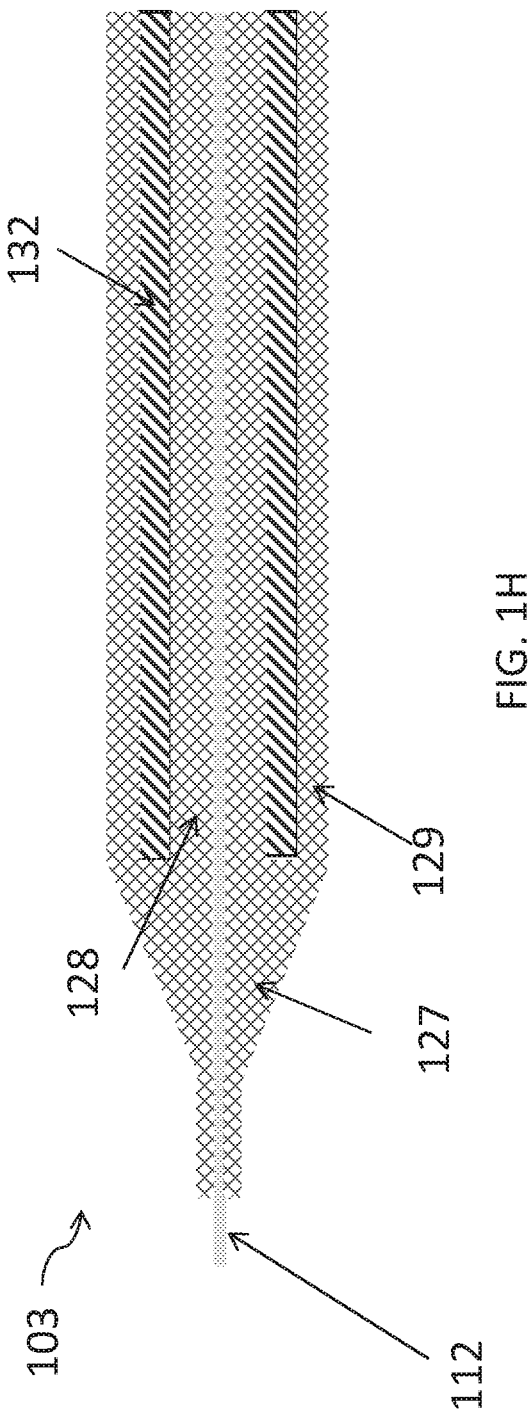
FIG. 1H is a schematic drawing of a cross-sectional side view of the microsensor of FIG. 1G.

FIGS. 1G and 1H show a top view and a cross-sectional side view of another exemplary microsensor of the presently disclosed subject matter wherein a portion of the tip end is covered by a coating layer (e.g., the polymer material and/or any other materials). Microsensor 103 comprises a first length 105 and a second length 107. First length 105 includes tip end 110 of electron conducting fiber 112 and tapered section 120 further comprising polymer coating 127 having a tapering outer surface. A portion 135 of tip end 110 is covered by polymer coating 127 and a terminal end 137 of tip end 110 is free of polymer coating 127. Second length 107 includes support section 130. Polymer coating 127 extends into support section 130, which comprises outer polymer coating 129, which is present over the outer surface of support material 132. Inner polymer coating 128 is present between the surface of fiber 112 and the inner surface of support material 132.

IV. Molds

In some embodiments, the presently disclosed subject matter provides a mold for preparing a microsensor. The mold can be, for example, generally cuboid in shape, having a square or rectangular top and bottom surface and which is generally wider and longer than it is thick. In some embodiments, the mold comprises at least one channel having a first end and a second end and channel walls, wherein the first end, the second end and channel walls are configured according to predetermined geometries. Representative geometries are disclosed herein, which can comprise particular dimensions and channel section configurations. For example, the mold can comprise at least one channel or groove in the top surface of the mold, wherein each channel includes at least one tapered section. The at least one channel is open at the top surface of the mold and open at least one side surface of the mold. The at least one channel can have a length ranging from about 10 mm to about 200 mm (e.g., 10, 15, 20, 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, or about 200 mm).

In some embodiments, each of the at least one channels can comprise at least two sections: (a) a first channel section adjacent to a side edge of the mold and having a first channel width; and (b) a second channel section adjacent to the first channel section, wherein the second channel section has channel walls that taper from a first end of the second channel section adjacent to the first channel section to a second end of the second channel section, such that the width of the first end of the second channel section is larger than the width of the second end of the second channel section.

In some embodiments, each of the at least one channels can comprise at least three sections: (a) a first channel section adjacent to a side edge of the mold and having a first channel width; (b) a second channel section adjacent to the first channel section; and (c) a third channel section adjacent to the second channel section, wherein the third channel section has a third channel width; wherein the third channel width is smaller than the first channel width, and wherein the second channel section has channel walls that taper from an end (i.e., the end adjacent to the second channel section) of the first channel section to an end (i.e., the end adjacent to the second channel section) of the third channel section.

In some embodiments, the first channel section has a length of about 15 mm or longer (e.g., about 15, 20, 25, 30, 35, 40, 45, 50, 55, 60, 65, 70, or 75 mm or longer). In some embodiments, the first channel section has a length ranging from about 15 mm to about 100 mm (e.g., about 15, 20, 25, 30, 35, 40, 45, 50, 55, 60, 65, 70, 75, 80, 85, 90, 95, or 100 mm). In some embodiments, the second channel section has a length of about 5 mm or longer. In some embodiments, the second channel section has a length ranging from about 5 mm to about 50 mm (e.g., about 5, 10, 15, 20, 25, 30, 35, 40, 45, or 50 mm). In some embodiments, the second channel section has a length of greater than 50 mm. Thus, in some embodiments, the second channel section has a length of between about 50 mm and about 200 mm (e.g., about 50, 60, 70, 80, 90, 100, 110, 120, 130, 140, 150, 160, 170, 180, 190, or 200 mm). In some embodiments, the third channel section has a length of about 3 mm or longer. In some embodiments, the third channel section has a length ranging from about 3 mm to about 50 mm (e.g., about 3, 5, 10, 15, 20, 25, 30, 35, 40, 45, or 50 mm).

In some embodiments, the first channel width can be between about 200 µm and about 1000 µm (e.g., about 200, 300, 400, 500, 600, 700, 800, 900, or about 1000 µm). In some embodiments, the first channel width is between about 500 and about 700 µm. In some embodiments, the first channel width is about 640 µm. The width of the first end of the second channel section can be between about 200 µm and about 1000 µm (e.g., about 200, 300, 400, 500, 600, 700, 800, 900, or about 1000 µm). In some embodiments, the width of the first end of the second channel section is between about 500 and about 700 µm. In some embodiments, the width of the first end of the second channel section is about 640 µm.

In some embodiments, the width of the second end of the second channel section is between about 10 µm and about 200 µm (e.g., about 10, 20, 30, 40, 50, 60, 70, 80, 90, 100, 110, 120, 130, 140, 150, 160, 170, 180, 190, or about 200 µm). In some embodiments, the width of the second end of the second channel section is about 150 µm.

In some embodiments, the third channel width is between about 10 µm and about 200 µm (e.g., about 10, 20, 30, 40, 50, 60, 70, 80, 90, 100, 110, 120, 130, 140, 150, 160, 170, 180, 190, or about 200 µm). In some embodiments, the third channel width is about 150 µm.

In some embodiments, the mold comprises two or more channels. In some embodiments, the mold can comprise two or more channels positioned at regular intervals along one or both longitudinal sides of the top surface of a mold with a rectangular top surface. In some embodiments, the mold comprises 20 channels per side. In some embodiments, the mold can comprise at least 8, 10, 12, 14, 16, 18, 20, 22, 24, 26, 28, 30, 32, 34, 36, 38, 40, 42, 44, 46, 48 or more channels. In some embodiments, the mold can comprise 40 channels.

In some embodiments, the mold is produced via a 3D printing process. As described hereinabove, 3D printing using CAD can provide customizability, as well as precise and small channel features.

The mold can be prepared from any suitable material. Generally the mold comprises a polymeric material, such as a material generally compatible for use as a print material in a 3D printer. In some embodiments, the mold comprises a material selected from the group comprising an acrylonitrile butadiene styrene terpolymer (ABS), nylon (polyamide) resin, metal such as stainless steel, ceramic, and combinations thereof. Indeed, most of the commercially available 3D printing materials are mixes of a variety of components, as would be understood by one of ordinary skill in the art upon a review of the instant disclosure.

Figure 2A:
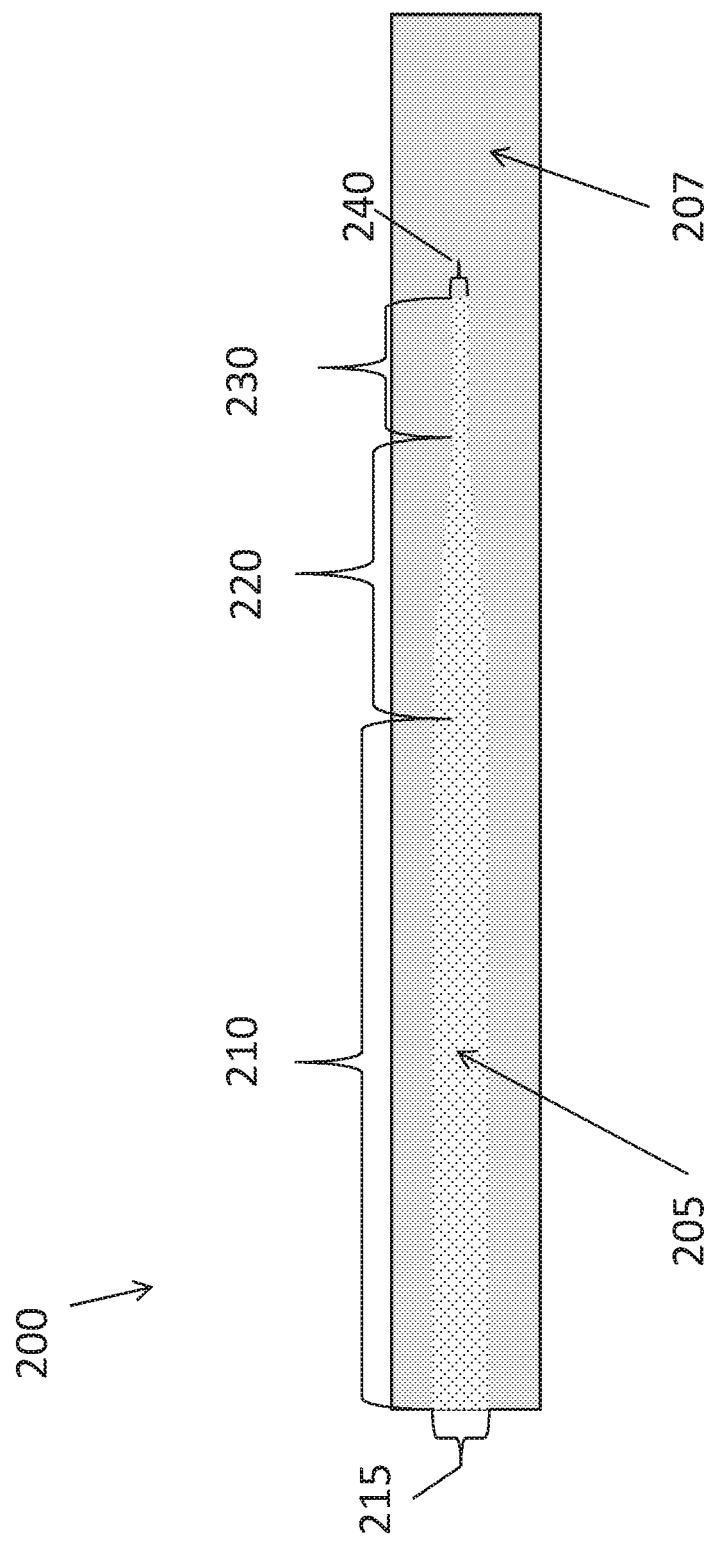
FIG. 2A is a schematic drawing of a close up top view of a single channel in a three-dimensional (3D) printed plastic mold for the production of a microsensor comprising an electron conducting fiber.

FIG. 2A shows an exemplary channel of a mold of the presently disclosed subject matter. More particularly, FIG. 2A shows mold 200 comprising channel 205 in mold top surface 207. Channel 205 has three sections. First channel section 210 includes end 215 open to a side of mold 200. Adjacent to first channel section 210 is second channel section 220, which has channel walls that taper, optionally evenly, from first channel section 210 to third channel section 230. Third channel section 230 includes end 240.

Figure 2C:
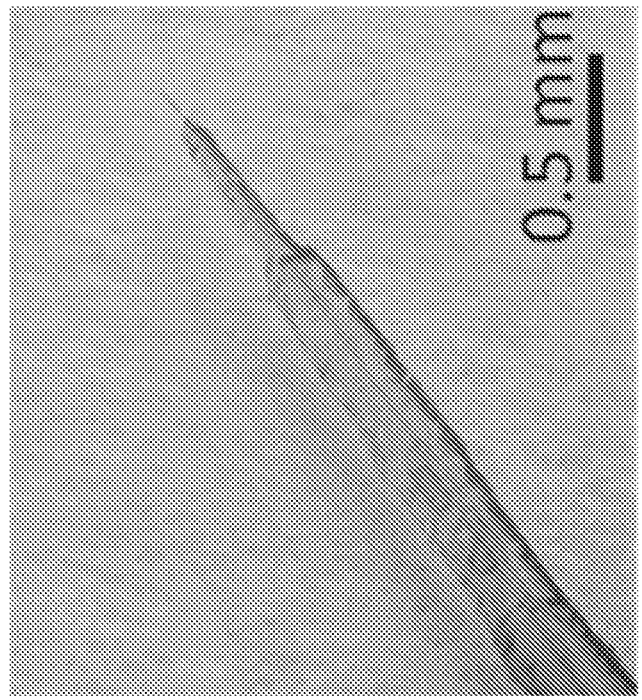
FIG. 2C is a microscopy image of a polyimide-insulated carbon fiber microelectrode prepared using the mold channel shown in FIG. 2B. The scale bar in the lower right hand corner represents 0.5 millimeters (mm).
Figure 2B:
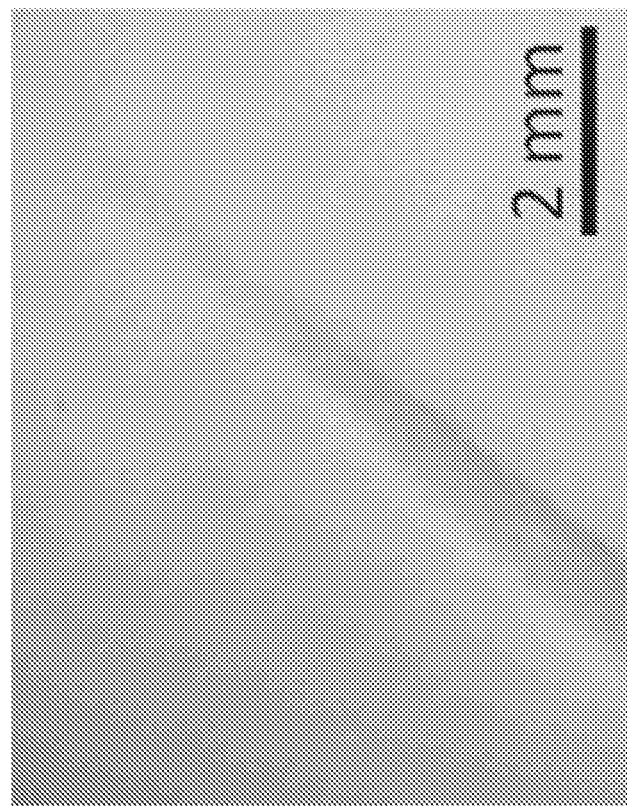
FIG. 2B is a microscopy image of a tip section of a mold channel of a three-dimensional (3D) printed mold of the presently disclosed subject matter. The scale bar in the lower right hand corner represents 2 millimeters (mm).
Figure 2D:
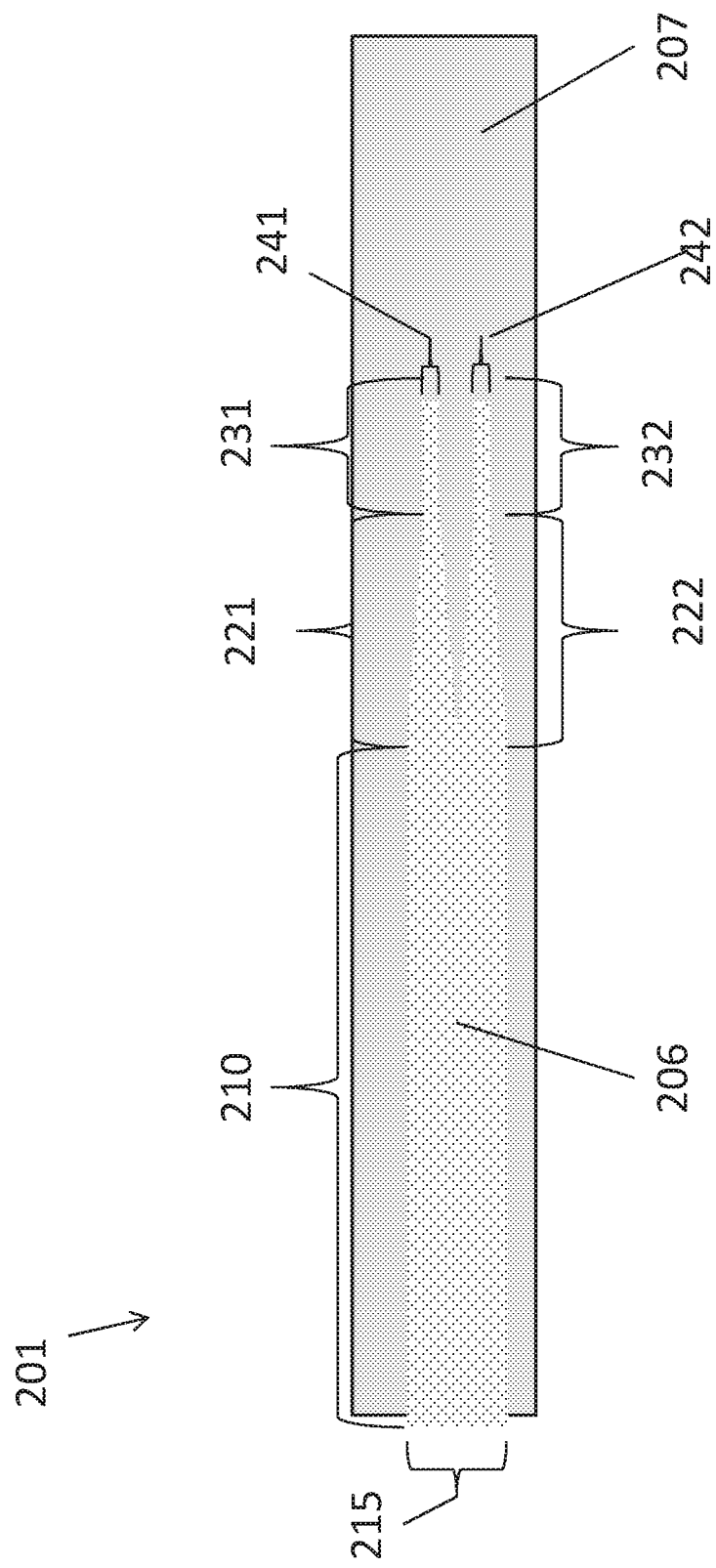
FIG. 2D is a schematic drawing of a close up top view of a single channel in a three-dimensional (3D) printed plastic mold for the production of a microsensor comprising two electron conducting fibers.

FIG. 2D shows an exemplary channel for preparing a microsensor comprising two electron conducting fibers that have separate tip ends. FIG. 2D shows mold 201 comprising channel 206 in mold top surface 207. Channel 206 has first channel section 210 that includes end 215 open to a side of mold 201. Channel 206 includes two tapered second channel sections 221 and 222 and two third channel sections 231 and 232 with channel ends 241 and 242, respectively. Mold 201 is suitable for use in producing a microsensor wherein part of one electron conducting fiber can be present in sections 221 and 231 during preparation of the microsensor, and part of a second electron conducting fiber can be present in sections 222 and 232, while parts of both fibers can be present in section 210.

V. Methods of Preparing Microsensors

In some embodiments, the presently disclosed subject matter provides a method of producing a microsensor. Generally, the method can comprise providing a mold comprising at least one channel having at least one tapered section, such as a mold as described hereinabove. For example, in some embodiments, the mold comprises at least one channel having a first end and a second end and channel walls, wherein the first end, the second end and channel walls are configured according to predetermined geometries. Representative geometries are disclosed herein, which can comprise particular dimensions and channel section configurations.

In some embodiments, each of the at least one channels can comprise at least two sections: (a) a first channel section adjacent to a side edge of the mold and having a first channel width; and (b) a second channel section adjacent to the first channel section, wherein the second channel section has channel walls that taper from a first end of the second channel section adjacent to the first channel section to a second end of the second channel section, such that the width of the first end of the second channel section is larger than the width of the second end of the second channel section. In some embodiments, the mold is a mold prepared via a 3D printing method.

In some embodiments, the mold comprises at least one channel comprising at least three sections: (a) a first channel section adjacent to a side edge of the mold and having a first channel width; (b) a second channel section adjacent to the first channel section; and (c) a third channel section adjacent to the second channel section; wherein the third channel section has a third channel width that is smaller than the first channel width; and wherein the second channel section has channel walls that taper from an end of the first channel section to an end of the third channel section. In some embodiments, the mold is a mold prepared via a 3D printing method.

Continuing, the method can further comprise: (b) inserting an electron conducting fiber into a support material; (c) placing the support material in a channel in the mold, e.g., such that the support material is present in the first channel section and wherein a support material-free length of the fiber is present the second or second and third sections of the channel; (d) filling the channel with a polymeric material (e.g., a polymeric resin or solution of uncured polymer); (e) curing the polymeric material to provide a microsensor; and (f) removing the microsensor from the mold.

For example, step (b) can comprise inserting an electron conducting fiber into a glass capillary or metal cannula, e.g., such that one or both ends of the fiber extend out of the ends of the capillary or cannula, and placing the capillary or cannula in the first section of the channel, such that the fiber extends into the second or second and third sections of the channel. Lengths of the fiber can also extend beyond one or both ends of the channel. In some embodiments, the support material can be placed so that it fills the full length of the first channel section. In some embodiments, the support material is placed so that there is no support material in the part of the first channel section nearest the second channel section.

In some embodiments, the polymeric material (e.g., a polymer resin of an electronically insulating polymer) is a thermosetting polymeric material, and the curing is performed by heating the mold (e.g., in an oven). Alternatively, curing can be performed via a photochemical process, e.g., by exposing the mold to UV light. In some embodiments, the mold is heated to a first temperature for a first period of time. In some embodiments, the first temperature is about 80° C. or more. In some embodiments, the first temperature is between about 100° C. and about 150° C. (e.g., about 100, 105, 110, 115, 120, 125, 130, 135, 140, 145, or about 150° C.). In some embodiments, the first temperature is about 150° C. In some embodiments, the first period of time is between about 5 minutes and about 60 minutes (e.g., about 5, 10, 15, 20, 25, 30, 35, 40, 45, 50, 55, or about 60 minutes). In some embodiments, the first period of time is about 30 minutes. In some embodiments, the method further comprises adding additional polymer resin to the channel following the first period of time and then curing the additional polymer resin. The additional polymer resin can be cured by heating, e.g., at a second temperature for a second period of time. In some embodiments, the second temperature and/or the second period of time are the same temperature and/or time as the first temperature and the first period of time.

In some embodiments, the method further comprises sealing an end of the microsensor adjacent to the first channel section with a resin, such as, but not limited to an epoxy resin or paraffin. In some embodiments, the removing is performed by removing the microsensor using a tweezers or a small spatula. In some embodiments, the removing is performed by bending the mold and then removing the microsensor, e.g., with a tweezers. In some embodiments, the method can further comprise trimming exposed fiber (e.g., exposed fiber that extends out of the end of the second or third channel section that corresponds to the end of the channel) to a desired length prior to or after the microsensor is removed from the mold.

The presently disclosed method is suitable for batch preparation of microsensors. Thus, in some embodiments, the method comprises providing a mold with a plurality of channels and preparing a plurality of microsensors by preparing a microsensor in each of the plurality of channels at the same time. Thus, for example, a plurality of support materials with inserted electron conducting fibers can be provided and each support material can be placed into a separate channel in a mold such that the support material is present in the first channel section and a length of exposed fiber is present in the second and third sections of the channel. Then, each of the channels can be filled with a polymeric material (e.g., a polymeric resin or a solution of uncured polymer) and the polymeric material cured (e.g., by placing the entire mold in a heated oven for a period of time), thereby simultaneously curing the polymer coating of each of the plurality of microsensors. Then the microsensors can be removed from the mold. In some embodiments, 8, 10, 12, 14, 16, 18, 20, 22, 24, 26, 28, 30, 32, 34, 36, 38, 40, or more microsensors can be made at a time.

In some embodiments, the same mold is reused one or more times to make additional microsensors, i.e., using one or more channels in which a microsensor has been previously prepared. In some embodiments, the mold is reused 2, 3, or 4 times.

Figure 3:
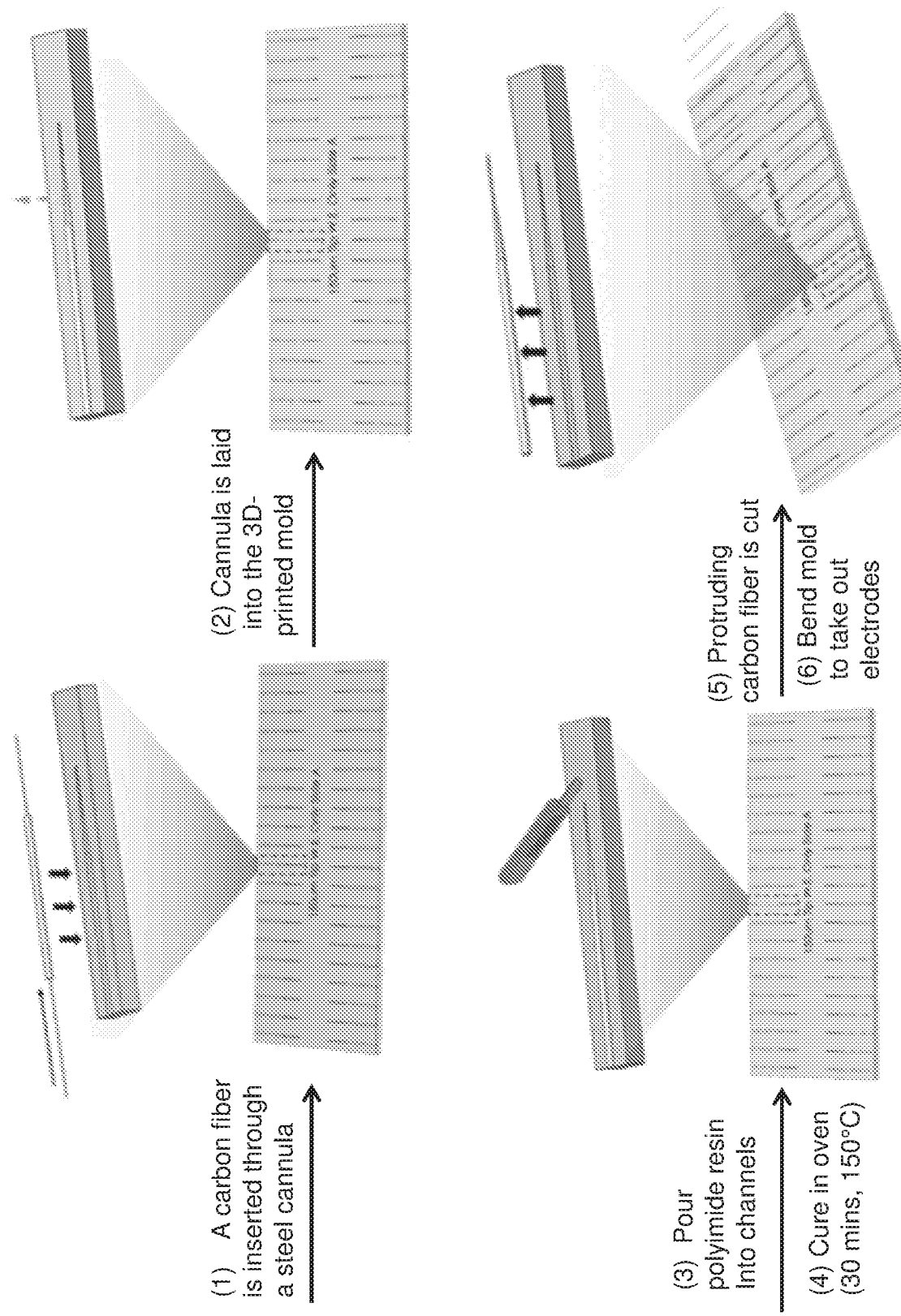
FIG. 3 is a schematic drawing showing a process for preparing microelectrodes using a three-dimensional (3D) printed mold according to one embodiment of the presently disclosed subject matter.

In some embodiments, the presently disclosed subject matter provides a microsensor prepared according to a method as described herein. FIG. 3 shows a schematic drawing of an exemplary embodiment of the presently disclosed method. As shown at the left-hand side of FIG. 3, in a first step, a carbon fiber is inserted through a metal cannula. The cannula is then laid into a channel of a 3D printed mold comprising a plurality of channels. If desired, additional cannulas with inserted carbon fibers can be laid into one or more (or each) of the other channels in the mold. In a third step, polyimide resin is poured into the channels and the resin is cured by placing the mold into an oven for 30 minutes at 150° C. In some embodiments, the amount of polymer material used ranges from about 0.02 to about 0.05 milliliters (ml), including 0.03 and 0.04 ml. The polymer material, e.g. polymer resin, can be poured into the second or second and third sections of the channel. In some embodiments, a portion of the tip end of the fiber is out of the second channel section or second and third channel section, so the polymer material does not cover all of the tip end of the fiber. In some embodiments, the second end of the second channel section and third channel are narrow enough such that when the fiber is present in the channel the fit is secure enough to substantially preclude polymeric material from flowing into the channel section.

After curing, the protruding carbon fiber is cut. Then the mold is bent (e.g., manually bent) slightly and the cured electrode is removed from the channel. In some embodiments, one or more steps of the method can be performed robotically and/or using an assembly line.

VI. Methods of Detecting Electrical Activity and/or Biological Molecules

In some embodiments, the presently disclosed subject matter provides a method of detecting electrical activity, e.g., in vitro or in vivo, wherein the method comprises providing a microsensor comprising an elongated body comprising an electron conducting fiber and a tapered, insulated section and/or prepared using a 3D printed mold, contacting the microsensor to a sample; and detecting an electrical signal using the microsensor. In some embodiments, the sensor can be connected to a waveform generator, a potentiostat, a galvanostat, an amplifier, a breakout box, and/or other hardware (e.g., a computer or microprocessor and/or computer interface cards). In some embodiments, the sample is a biological sample, such as, a cell, a tissue, an organ, a cell extract, or an extracellular fluid. In some embodiments, the sample comprises a cell, a tissue, or an organ. In some embodiments, sample comprises a brain, nerve or heart cell, brain, muscle, or heart tissue, or a brain or brain substructure or a heart. In some embodiments, the sample is an in vivo sample.

The microsensor can detect a chemical or physical change in a sample by converting the change to an electrical signal (e.g., a current, voltage. or resistance). In some embodiments, detecting the electrical activity comprises detecting brain and/or nerve activity. In some embodiments, the brain and/or nerve activity can be detected as a response to a drug, or to another stimulus (e.g., a physical activity, music or another auditory stimulus, a picture or another visual stimulus, etc.).

In some embodiments detecting the electrical activity detects the presence and/or amount of a biological molecule, such as a neurotransmitter or a metabolite thereof. For example, the neurotransmitter can be a biogenic amine, such as, but not limited to, dopamine, histamine, epinephrine (i.e., adrenaline), norepinephrine (i.e., noradrenaline), serotonin, melatonin, a phenethylamine, a thyronamine, tryptamine, and the like. In some embodiments, a current is detected as the result of a redox reaction of a molecule (e.g., the biological molecule being detected) at an electroactive surface (i.e., the surface of a non-insulated portion of the electron conducting fiber) of the sensor, which can result in electron transfer in an amount proportional to the amount of the molecule. Thus, in some embodiments, the amount of current detected by the electrode indirectly provides a measure of the quantity of the molecule.

In some embodiments, the microsensor is configured for use as a microelectrode and an electrical stimulus (e.g., a potential or electrical pulse) can be applied to a sample using the sensor. The sensor can also be configured as part of an electrochemical cell (e.g., as a working, reference or counter electrode or as a working electrode wherein the sensor itself comprises at least two electron conducting fibers that can act as electrodes). The term "working electrode" (or "sensing electrode") can refer to an electrode that interacts with an analyte dissolved or suspended in a conducting medium, such as water, blood, plasma, serum, lymph, interstitial fluid and the like. The interaction of the working electrode with an analyte produces a change in voltage, current, charge, impedance, etc., that can be transmitted, for example, to a digital or analog measuring device such as an ammeter, voltmeter or electrometer. The term "reference electrode" can refer to an electrode that can serve as a reference point with respect to which the voltage at the working electrode is measured or applied. When incorporated into an electrical circuit containing a potentiostat, the reference electrode can help provide for an exact potential difference to be maintained between itself and the working electrode, by varying the potential difference between the working electrode and the counter electrode.

When a voltage is applied between the working electrode and the counter electrode, the potential can be used to drive an electrochemical reaction at the surface of the working electrode. The output current produced from the electrochemical reaction at the working electrode is balanced by a current flowing in the opposite direction at the counter electrode. The sensor output current resulting from the electrochemical reaction can amplified and can be converted to a voltage in order to display the output signal or a transduced output signal on a recording device.

In some embodiments, the biological molecule is a neurotransmitter. In some embodiments, the detection is via a cyclic voltammetry technique, such as fast-scan cylic voltammetry (FSCV). In cyclic voltammetry, the current response over a range of potentials (a potential window) is measured, starting at an initial value and varying the potential in a linear manner up to a pre-defined limiting value. At this potential, referred to as a switching potential, the direction of the potential scan is reversed, and the same potential window is scanned in the opposite direction. The data is then plotted as current (i) vs. potential (E). The current increases as the potential reaches the oxidation/reduction potential of a given redox reaction, but then falls off as the concentration of the analyte is depleted. Alternatively, the detection can be performed via another electrochemical technique, such as amperometry, differential pulse voltammetry (DPV), linear sweep voltammetry, chronocoulometry, chronoaperometry, chronopotentiometry, or controlled potential coulometry.

In some embodiments, the detecting is performed in vivo and the microsensor is present in a tissue of a living subject. In some embodiments, for example, the microsensor is inserted into a brain tissue of a subject (e.g., a mammalian subject, such as, but not limited to a mouse, rat, or other rodent; a rabbit; a cat, a dog; a monkey; an ape; or a human). In some embodiments, the subject is a subject who has been diagnosed with or is suspected of having a disease or condition associated with problems related to neurotransmission and/or nerve cell dysfunction, such as, but not limited to, Parkinson's disease, Huntington disease, Alzheimer's disease, epilepsy, attention deficit hyperactivity disorder (ADHD), amyotrophic lateral sclerosis (ALS), depression, schizophrenia, anxiety disorders, chronic pain and/or addiction. In some embodiments, the detecting is performed as part of monitoring the disease or disease treatment.

In some embodiments, the presently disclosed microsensors can be configured for use in a method comprising electrically stimulating a tissue or organ, e.g., in subjects suffering from a disease or condition associated with problems related to neurotransmission and/or nerve cell dysfunction. In some embodiments, electrical activity and/or a biological molecule (e.g., a neurotransmitter) can be detected in combination with electrically stimulating the tissue or organ. For example, the stimulation can result in a change in the concentration of a biological molecule and the change in concentration can be detected by a sensor.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Electrode Fabrication

Molds were designed in AUTODESK INVENTOR™ Professional 2014 Student Edition (Autodesk, Inc., San Rafael, Calif., United States of America), converted to a .STL file and printed. Molds were printed using a Stratasys Connex 500 Model 1 Poly-Jet 3D printer (Stratasys Ltd., Eden Prairie, Minn., United States of America). The printer has 8 print heads with 96 nozzles per print head. The molds were printed with Rigid Opaque black polymer build material comprising mainly ABS (i.e., VeroBlackPlus RGD875, Stratasys Ltd., Eden Prairie, Minn., United States of America). This material combines dimensional stability, fine detail and is suitable for rapid tooling. However, other materials with different curing temperatures, stiffness and colors could also be used.

The print heads were heated to 60° C. for use with the Rigid Opaque material and the Z axis resolution with the material was 30 micron. Water jets were used to remove the support material. The resulting mold provided a non-stick surface for polyimide resin, resulting in the ability to fabricate removable electrodes inside a fitting whose dimensions were well documented.

More particularly, for microelectrode fabrication, individual carbon fibers (7 µm in diameter, T650, Cytec Engineering Materials, West Patterson, N.J., United States of America) were aspirated into 0.68 mm ID×1.2 mm OD glass capillaries. The fibers and capillaries were laid manually into each channel of the 3D printed mold, and a polyimide sealing resin (Grace Davison Discovery Sciences, Deerfield, Ill., United States of America) was poured into the channels. The resin was allowed to cure for 30 minutes at 150° C., removed from the oven for an additional application of a resin layer, and then cured for another 30 minutes at 150° C. Carbon fiber was trimmed by scalpel under a stereomicroscope to about 150 µm in length. The microelectrode was removed from the mold by bending the mold and removing the microelectrode using a tweezers.

Discussion: Polyimide-insulated microelectrodes were prepared using a 3D printed mold. FIG. 1 shows a schematic drawing of an exemplary single channel in an exemplary 3D printed mold of the presently disclosed subject matter. The mold design is based on a channel with sharp tips that are about 150 µm in width/diameter and 3 mm long. The tips connect to a tapered section that is 5 mm long, making the total polyimide section about 8 mm long. This length is longer than the typical penetration depth (i.e. about 4.5-5 mm) for the caudate putamen. However, the length can be customized for other brain regions or applications if desired. There is also a 15 mm section designed for microelectrode support, such as a cannula needle. Cannula needles made of stainless steel are widely used for neuroscience studies and are safer for brain insertion than glass capillaries. See Heien et al., 2005. A 23 gauge cannula needle was used as the connector, with an inner diameter (ID) of 0.34 mm and an outer diameter (OD) of 0.64 mm, which is about half the outer diameter of conventionally used glass capillaries (i.e., about 1.2 mm). FIG. 2B shows an image of an actual mold channel, while FIG. 2C shows an electrode after fabrication. In exemplary embodiments, the mold design included 24 or 40 electrode channels per side (48 or 80 total electrodes per mold). The number of channels can be customized by changing the computer-aided design (CAD) parameters.

The process of making the polyimide-insulated CFMEs is shown in FIG. 3. An individual carbon fiber is inserted through a 23 gauge cannula needle and the needle was laid in a wide part of a mold channel. Polyimide resin was then poured into the mold channels, filling up the tapered and tip part and sealing it to the cannula. It took about 15 minutes to fill 24 channels and 20 minutes to fill 40 channels with polyimide resin, which was then cured for 30 minutes in an oven at 150° C. An additional layer of polyimide resin can be applied if desired and cured for another 30 minutes at 150° C. The protruding carbon fiber is then trimmed to make a cylindrical working electrode with a regulated length of exposed electroactive surface area, typically about 100-150 µm long. The process has the potential to be further automated, e.g., using robotics to lay the cannulas and/or pour resin, for the production of a larger number of electrodes. In addition, the length of the protruding fiber can be more closely controlled upon laying it in the channel.

Since the 3D printed mold of the present example is primarily made of ABS, it provides a non-stick surface for the polyimide resin. The use of this material provides for the removal of the polyimide-insulated CFMEs by simply bending the flexible polymer mold and removing the electrode using tweezers. The 3D printed mold was reused four times before the detail of the device began to deteriorate. Further the average cost of the materials for each electrode was less then 20 cents, with costs for a batch including only about $1 for the polyamide resin, less than 25 cents for the carbon fiber and about $18 for the mold of 40 channels. The total time cost for the fabrication of the 40 microelectrodes was less than 2 hours. Thus, the method appears to be useful as a cheaper alternative to currently available commercial neurochemical microsensors.

Example 2

Electrochemical Detection of Dopamine In Vivo using Polyimide-Insulated Microelectrode Electrochemical Instrumentation: Fast scan cyclic voltammetry (FSCV) was performed using a ChemClamp potentiostat (Dagan, Minneapolis, Minn., United States of America). The waveform was generated and data collected using a High Definition Cyclic Voltammetry (HDVC) breakout box and PCIe-6363 computer interface cards (National Instruments, Austin, Tex., United States of America). Electrodes were backfilled with 1 M potassium chloride (KCl) and a silver wire was inserted to connect the electrode with the potentiostat headstage. A triangle waveform was applied to the electrode from a holding potential of −0.4 V to 1.3 V and back at a scan rate of 400 V/x and a frequency of 10 Hz. A silver-silver chloride (Ag/AgCl) wire was used as the reference electrode. Samples were tested using a flow injection analysis system as previously described. See Keithley et al., 2011. Buffer and samples were pumped through the flow cell at 2 m:/min using a syringe pump (Harvard Apparatus, Holliston, Mass.).

Animals: 250-350 gram male Sprague-Dawley rats (Charles River Laboratories, Wilmington, Mass., United States of America) were anesthesized with urethane (1.5 mg/kg i.p.). The scalps were shaved and 0.25 mL bupivicaine (0.25% solution) was given subcutaneously. The working electrode was implanted in the caudate putamen (in mm from bregma: AP+1.2, ML+2.0, and DV−4.5 to 5.0), the stimulating electrode in the substantia nigra (AP−5.4, ML+1.2, and DV−7.5), and the Ag/AgCl reference electrode in the contralateral side of the brain. The DV placement was adjusted downward until a robust dopamine signal was measured. The polyimide-insulated carbon-fiber electrode was inserted into the brain and the FSCV waveform applied for 30 minutes to allow the electrode to stabilize. Stimulated release was electrically evoked using biphasic stimulation pulses (300 μA, 30 to 120 pulses, 60 Hz).

Figure 4A:
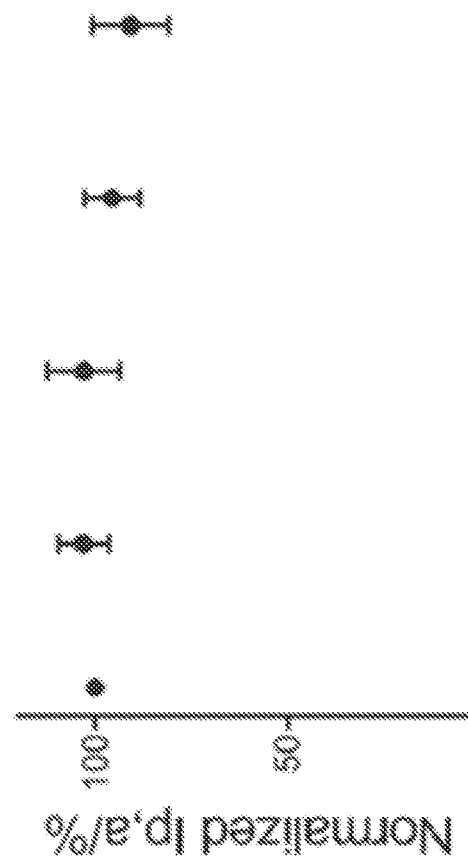
FIG. 4A is a graph showing the oxidation current measured with a polyimide-insulated carbon fiber microelectrode immersed in buffer with 1 µM dopamine over a 4 hour time period. Waveform was continually applied and measurements were taken every hour. Data were normalized to initial current values for peak oxidation of dopamine.
Figure 4B:
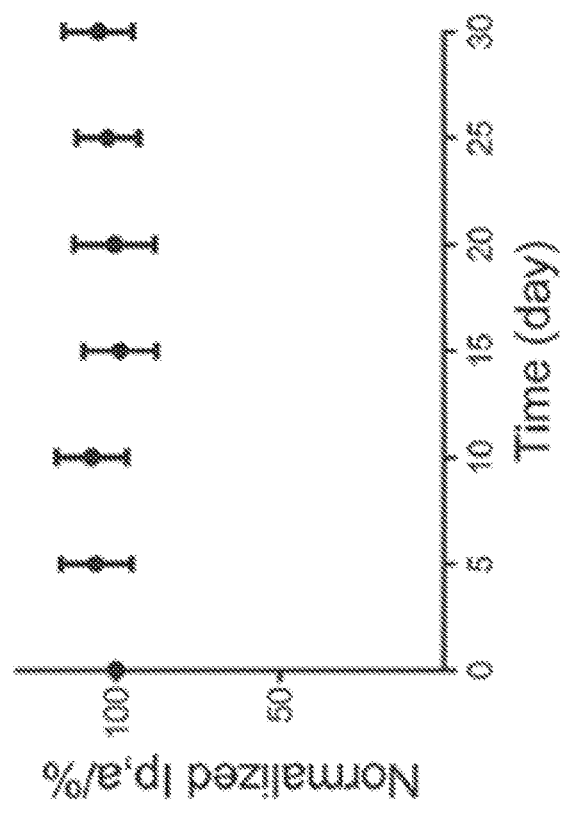
FIG. 4B is a graph showing the oxidation current measured with a polyimide-insulated carbon fiber microelectrode immersed in buffer with 1 µM dopamine take over a month long time period every 5 days. Data were normalized to initial current values for peak oxidation of dopamine.

Results: Dopamine was used as an exemplary biomolecule to test the detection ability of the polyamide resin sealed carbon fiber microsensors. Dopamine is an important neurotransmitter in the mammalian central nervous system, both in vitro and in vivo. FIG. 4A shows that the oxidation current for dopamine does not change over several hours of continuous FSCV using a 150 μm long cylindrical CFME made with a 3D printed mold and a polyimide insulating method. During this test, the waveform was continuously applied to the electrode while the electrode was immersed in a buffer solution. Thus, the microsensors are stable for continuous use over a typical time period for an in vivo stimulated release experiment. See Zachek et al., 2010. In addition, shelf stability was tested over a month time period. No change in oxidation current or temporal resolution was detected throughout the month long test period. See FIG. 4B. Thus, the microelectrodes are stable enough to warrant batch fabrication, as the electrodes can be pre-fabricated and stored until needed.

Figure 5A:
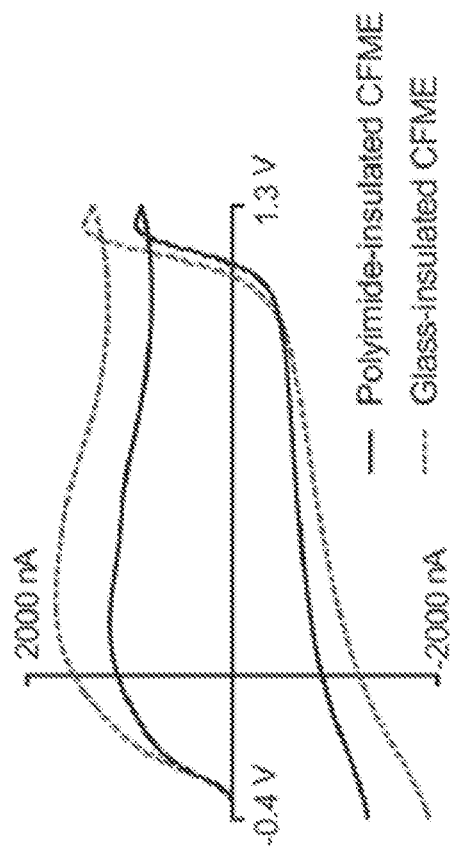
FIG. 5A is a graph showing an exemplary background subtracted cyclic voltammagram (CV) of 1 µM dopamine at a polyimide-insulated carbon fiber microelectrode (CFME) (solid line). For comparison, an exemplary background subtracted CV is also shown for 1 µM dopamine at a glass-insulated (CFME) (dotted line).
Figure 5B:
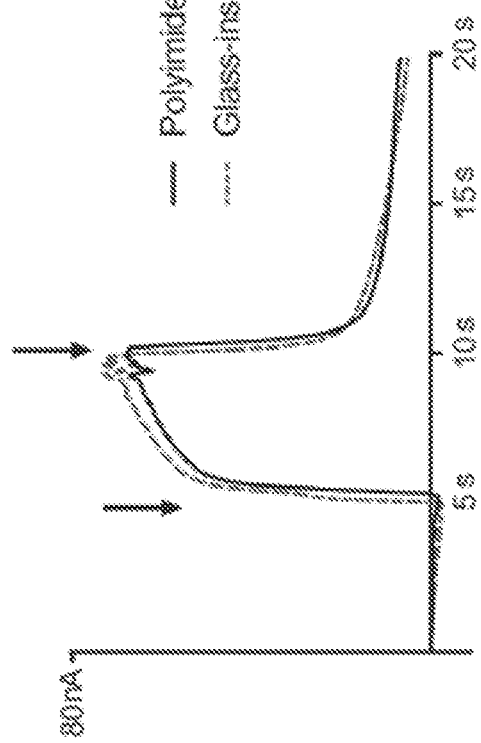
FIG. 5B is a graph showing the background charging currents for the same electrodes described in FIG. 5A in phosphate buffered saline (PBS) buffer.

The electrochemical properties of a polyimide-insulated CFME were compared to those of a traditional glass CFME. The background-subtracted cyclic voltammograms (CV) of 1 μM dopamine are similar, as expected given that the different CFMEs have the same length of protruding carbon fiber (i.e., 150 μm). See FIG. 5A. The oxidation peak for dopamine is not statistically different for glass-insulated CFMEs (66±3 nA, n=4) and polyimide-insulated CFMEs (64±2 nA, n=4, t-test, p=0.64). Thus, neither exposure to the polymer 3D printed mold nor the presence of the insulting polyimide appears to disturb the reaction of dopamine at the carbon surface. However, the polyimide-insulated CFMEs have smaller background currents (1100±100 nA, n=4) than glass-insulated CFMEs (1570±50 nA, n=4; t-test, p=0.0063). See FIG. 5B. Without being bound to any one theory, it is believed that the larger background current of the glass-insulated electrodes is due to the additional capacitance of the glass, which has a dielectric constant of 6 compared to the dielectric of polyimide, which is 3. See Maier, 2001. The thicknesses of the insulations are also different, with thinner glass than polyimide. Thus, it is possible that ions could conduct through the glass. But, despite the differences in background charging currents, the dopamine oxidation current of the electrode is not dependent on the type of insulation.

Figure 5C:
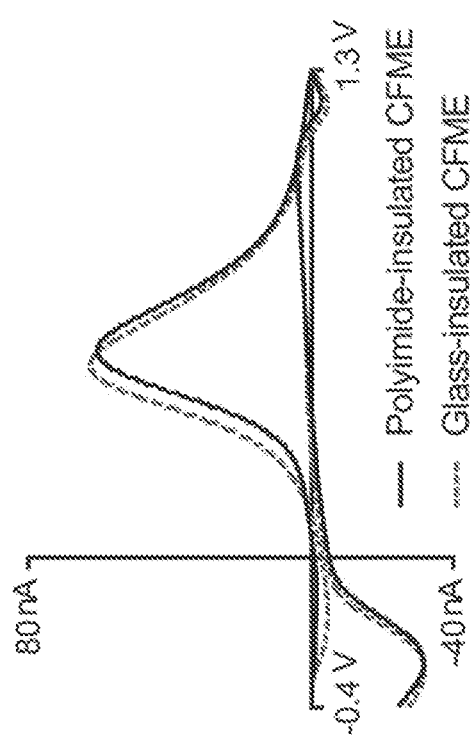
FIG. 5C is a graph showing current versus time plots for the electrodes described for FIG. 5A during a flow injection analysis experiment. The first arrow indicates the injection of a dopamine bolus. The second arrow shows when the flow is switched back to phosphate buffered saline (PBS) buffer.

FIG. 5C shows the temporal response of the CFMEs to a bolus of dopamine. The temporal response is not dependent on the type of insulation. Although the response is not perfectly square due to adsorption/desorption kinetics (see Bath et al., 2001), the consistent time response suggests that the polyimide-insulated CFMEs are well insulated and that the polyimide is not rough at the end, trapping dopamine near the electrode surface.

Figure 6A:
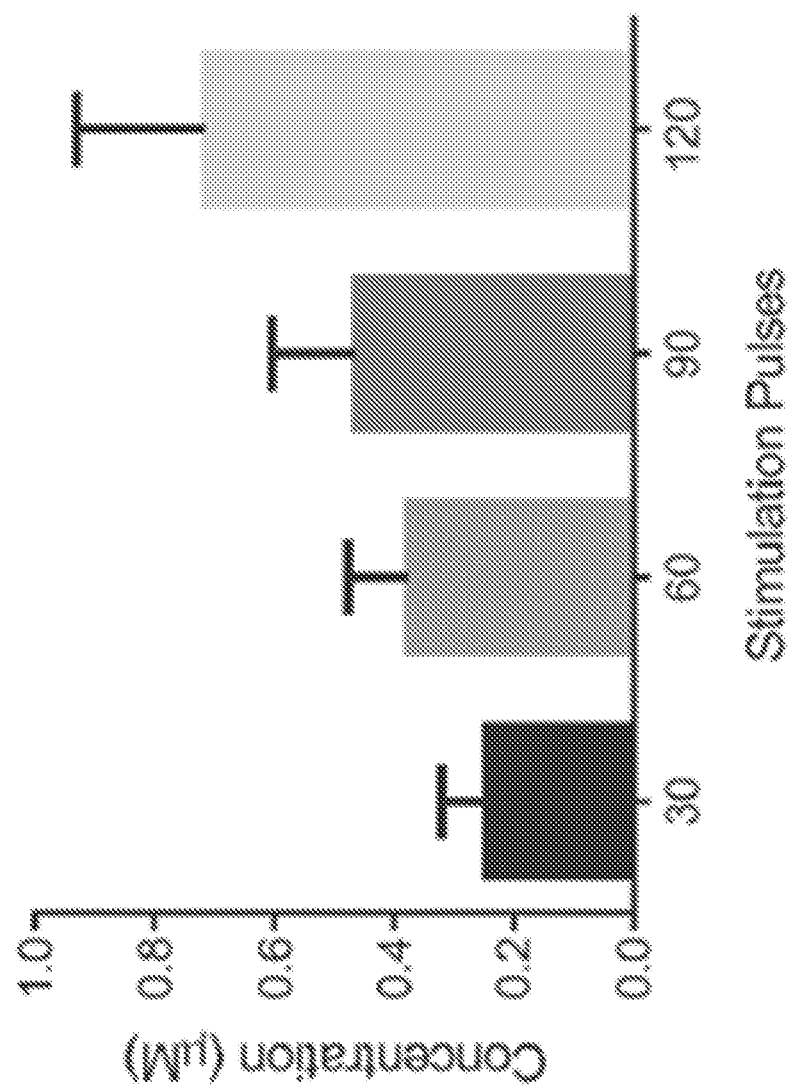
FIG. 6A is a graph showing the concentration (micromolar (µM)) of dopamine detected in vivo using polyimide-insulated carbon fiber microelectrodes (CFME) after different numbers of stimulated pulses. The concentration data is based on the conversion of peak cyclic currents recorded at after different numbers of stimulated pulses using post calibration factors. The data is based on data from four rats.
Figures 6B, 6C:
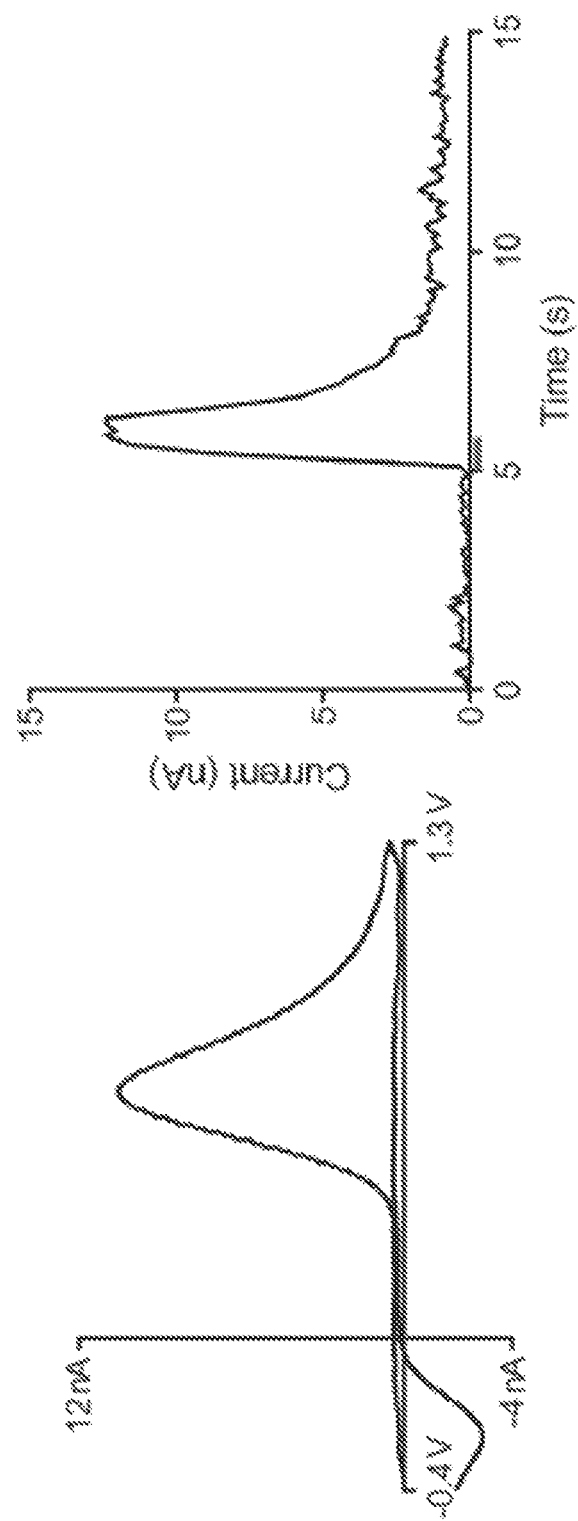
FIG. 6B is a plot showing an exemplary cyclic voltammogram (CV) of stimulated dopamine release detected in vivo using polyimide-insulated carbon fiber microelectrodes (CFME) placed in the caudate putamen with stimulation pulse trains of 60 pulses at 60 Hertz (Hz).
FIG. 6C is a plot showing an associated current (nanoampere (nA)) versus time (seconds (s)) for dopamine detection in vivo at a polyimide-insulated carbon fiber nanoelectrode. The bar under the x-axis indicates the stimulation duration.

To further determine the applicability of the polyimide resin sealed carbon fiber microsensors as in vivo sensors, stimulated dopamine release was measured in anesthetized rats. Stimulation pulse trains were applied (300 μA, 120 pulses, 60 Hz) to the dopamine cell bodies, and the dopamine response was recorded by the polyimide-insulated CFMEs in the caudate putamen near the terminals. FIG. 6A shows dopamine concentrations recorded at different stimulated pulses by the polyimide-insulated CFMEs (n=4 rats). Data was converted from peak currents to concentration based on post calibration factors. As seen in FIG. 6A, a higher number of pulses appears to elicit a larger release of dopamine on the microelectrode surface. The electrode is sensitive enough to detect dopamine release as low as 170 nM. FIGS. 6B and 6C show typical CV and current versus time plots of dopamine detection at a polyimide-insulated CFME in vivo.

REFERENCES

All references listed in the instant disclosure, including but not limited to all patents, patent applications and publications thereof, and scientific journal articles are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

Ambrosi, Moo and Pumera, *Adv. Functional Materials,* 2015, 26, 698-703.

Baik, *Front. Neural Circuits,* 2013, 7, 152.

Bath, Martin, Wightman and Anderson, *Langmuir,* 2001, 17, 7032-7039.

Baur, Kristensen, May, Wiedemann, and Wightman, Anal. Chem., 1988, 60, 1268-1272.

Cahill, Walker, Finnegan, Mickelson, Travis and Wightman, *Anal. Chem.,* 1996, 68, 3180-3186.

Chia and Wu, *J. Bio. Eng.,* 2015, 9, DOI: 10.1186/s13036-015-0001-4.

Clark, Sandberg, Wanat, Gan, Horne, Hart, Akers, Parker, Willuhn, Martinez, Evans, Stella and Phillips, *Nat. Methods,* 2010, 7, 126-129.

Earl, Sautter, Xie, Kruk, Kupsch, and Oertel, J. Neurosci. Methods, 1998, 85, 201-209.

Ewing, Dayton and Wightman, *Anal. Chem.,* 1981, 53, 1842-1847.

Garwon, Martin and Lunte, *Electrophoresis*, 2001, 22, 242-248.

Heien, Khan, Ariansen, Cheer, Phillips, Wassum and Wightman, *PNAS*, 2005, 102, 10023-10028.

Huffman and Venton, *Analyst*, 2009, 134, 18-24.

Jacobs, Ivanov, Nguyen, Zestos, and Venton, Anal. Chem., 2014, 86, 5721-5727.

Keithley, Takmakov, Bucher, Belle, Owesson-White, Parl and Wightman, *Anal. Chem.*, 2011, 83, 3563-3571.

Kishida, Sandberg, Lohrenz, Comair, Saez, Phillips and Montague, *PLoS One*, 2011, 6, e23291.

Lago, Yoshida, Koch and Navarro, *IEEE Trans. Biom. Eng.*, 2007, 54, 281-290.

Li, Liu, Sun, and Gao, Chem. Rev., 2015, 115, 7046-7117.

Lindsay and O'Hare, *Electrochimica Acta*, 2006, 51, 6572-6579.

Lücking, Sambale, Beutel, and Scheper, Eng. Life Sci., 2014, 51-56.

Maier, *Prog. Pol. Sci.*, 2001, 26, 3-65.

Navarro, Krueger, Lago, Micera, Stieglitz and Dario, *J. Periph. Nerv. Syst.*, 2005, 10, 229-258.

Ragones, Schreiber, Inberg, Berkh, Kósa, Freeman and Shacham-Diamand, *Sensors and Actuators B: Chem.*, 2015, 216, 434-442.

Ramsson, Cholger, Dionise, Andrus, Poirier and Curtiss, PLoS One, 2015, 10, e0141340.

Rengier, Mehndiratta, von Tengg-Kobligk, Zechmann, Unterhinninghofen, Kauczor and Giesel, *J. CARS*, 2010, 5, 335-341.

Robinson, Venton, Heien and Wightman, *Clin. Chem.*, 2003, 10, 1763-1773.

Rousche, Pellinen, Pivin, Williams, Vetter and Kipke, *IEEE Trans. Biom. Eng.*, 2001, 48, 361-370.

Sandron, Heery, Gupta, Collines, Nesterenko, Nesterenko, Talebi, Beirne, Thompson, and Wallace, Analyst, 2014, 139, 6343-6347.

Sokolov, Zhukov, Parfenov and Igoshin, *J. Surface Inv.*, 2013, 7, 178-180.

Sun, Zhang, Guo and Shao, *Anal. Chem.*, 2001, 73, 5346-5351.

Symes, Kitson, Yan, Richmond, Cooper, Bowman, Vilbrandt and Cronin, *Nature Chemistry*, 2012, 4, 349-354.

Zachek, Takmakov, Park, Wightman and McCarty, *Biosens. Bioelectron.*, 2010, 25, 1179-1185.

Zestos, Nguyen, Poe, Jacobs and Venton, *Sensors and Actuators B: Chem.*, 2013, 182, 652-658.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A microsensor comprising an elongated body, wherein said elongated body comprises a first end, a second end, and a core comprising an electron conducting fiber, further wherein the elongated body comprises a first length, wherein the first length comprises a tapered section and a tip end, wherein the tapered section comprises a polymer coating comprising an electronically insulating polymer material that covers the outer surface of the electron conducting fiber, further wherein a first end of the tapered section is directly adjacent to the tip end and wherein the thickness of the polymer coating is thicker at a second end of the tapered section than at the first end of the tapered section, thereby providing a tapered coating layer, and wherein the tip end comprises an uncoated portion, wherein the uncoated portion consists of an uncoated length of the electron conducting fiber, wherein said uncoated length comprises a terminal end of the electron conducting fiber and wherein said uncoated length is free of a coating layer.

2. The microsensor of claim 1, wherein the electron conducting fiber comprises a carbon fiber, a carbon nanotube fiber, a carbon nanotube yarn, a carbon nanotube grown metal microwire, a carbon nanospikes grown metal microwire, or a metal fiber.

3. The microsensor of claim 2, wherein the metal fiber comprises gold, platinum, tungsten, titanium, iridium or steel.

4. The microsensor of claim 1, wherein the polymeric material of the polymer coating is biocompatible.

5. The microsensor of claim 4, wherein the polymeric material comprises polyimide.

6. The microsensor of claim 5, wherein the polymeric coating further comprises a curing agent, a hydrogel, polyethyleneimine, and/or paraffin.

7. The microsensor of claim 1, wherein the tapered section has a length of about 5 millimeters (mm) or more.

8. The microsensor of claim 1, wherein the tip end has a length of between about 50 micrometers ($\mu$m) and about 50 millimeters (mm).

9. The microsensor of claim 8, wherein the tip end further comprises a coated section, wherein the coated section comprises a length of the electron conducting fiber covered by the electronically insulating polymer, and wherein the coated section is between the tapered section and the uncoated section of the tip end, and the tip end has a length of about 50 $\mu$m to about 50 mm.

10. The microsensor of claim 1, wherein the electron conducting fiber has a diameter of between about 7 $\mu$m and about 50 $\mu$m.

11. The microsensor of claim 10, wherein the electron conducting fiber has a diameter of about 7 $\mu$m.

12. The microsensor of claim 1, wherein the elongated body comprises a second length, wherein said second length comprises a support section, wherein said support section comprises a support material positioned over the outer surface of the electron conducting fiber.

13. The microsensor of claim 12, wherein at least one length of the support material is positioned over an inside polymer coating, under an outside polymer coating, or between an inside polymer coating and an outside polymer coating, wherein the inside and/or outside polymer coating comprise the same polymeric material as the polymer coating of the tapered section.

14. The microsensor of claim 12, wherein the support material comprises glass or metal.

15. The microsensor of claim 12, wherein the polymer coating of the tapered section extends into the second length of the elongated body, and the second length further comprises a non-support section positioned between the support section and the tapered section of the first length of the elongated body, wherein the non-support section comprises the polymer coating and the electron conducting fiber.

16. The microsensor of claim 15, wherein the non-support section has a length of about 3 mm or longer.

17. The microsensor of claim 15, wherein the thickness of the polymer coating is approximately the same over the entire length of the non-support section.

18. The microsensor of claim 12, wherein the support section has a length of about 15 mm or longer.

19. The microsensor of claim 12, wherein the outer diameter of the support section is about 1.5 mm or less.

20. The microsensor of claim 1, wherein the length of the elongated body is about 23 mm or longer.

21. The microsensor of claim 20, wherein the length of the elongated body is about 23 mm to about 200 mm.

22. The microsensor of claim 1, wherein the microsensor is produced using a mold prepared via a three dimensional printing method.

23. The microsensor of claim 1, wherein the elongated body comprises two or more electron conducting fibers.

24. The microsensor of claim 23, wherein each electron conducting fiber has a separate first length comprising a tapered section and a tip end.

25. A method of detecting electrical activity, wherein the method comprises providing a microsensor of claim 1; contacting the microsensor to a sample; and detecting an electrical signal using said microsensor.

26. The method of claim 25, wherein the sample comprises a cell, a tissue or an organ.

27. The method of claim 25, wherein the sample is a biological sample.

28. The method of claim 26, wherein the sample comprises brain or heart tissue.

29. The method of claim 25, wherein the microsensor is configured for use as a microelectrode, and wherein detecting the electrical activity detects a biological molecule.

30. The method of claim 29, wherein the biological molecule is a neurotransmitter.

31. A method of detecting a biological molecule, wherein the method comprises providing a microsensor of claim 1, wherein said microsensor is configured for use as a microelectrode; and detecting the biological molecule using the microsensor.

32. The method of claim 31, wherein the detecting is performed in vivo and wherein the microsensor is present in a tissue of a living subject.

33. The method of claim 32, wherein the microsensor is inserted in a brain tissue of a subject.

34. The method of claim 31, wherein the biological molecule is a neurotransmitter.

35. The method of claim 34, wherein the biological molecule is a biogenic amine.

36. The method of claim 35, wherein the biogenic amine is dopamine.

37. The method of claim 31, wherein detecting the biological molecule using the microsensor is via a cyclic voltammetry technique.

38. The method of claim 27, wherein the sample is an in vivo biological sample.

39. The microsensor of claim 1, wherein the second end of the tapered section is positioned at the second end of the elongated body.

40. The microsensor of claim 1, wherein the elongated body further comprises a second length, wherein the second end of the tapered section of the first length of the elongated body is positioned directly adjacent to the second length of the elongated body.

41. The microsensor of claim 1, wherein the tip end further comprises a coated section, wherein the coated section comprises a length of the electron conducting fiber covered by the electronically insulating polymer, and wherein the coated section is between the tapered section and the uncoated portion of the tip end.

42. The microsensor of claim 1, wherein the uncoated portion has a length of about 50 µm to about 300 µm.

43. A method of producing a microsensor, wherein said method comprises:
(a) providing a mold, wherein the mold comprises at least one channel comprising at least one channel section having a first end and a second end, wherein the at least one channel section tapers from the first end of the channel section to the second end of the channel section such that a width of the channel section at the second end of the channel section is narrower than a width of the channel section at the first end of the channel section;
(b) inserting an electron conducting fiber into a support material;
(c) placing the support material in the at least one channel in the mold, such that the support material is present in the at least one channel and wherein a length of the electron conducting fiber is present in the at least one channel;
(d) filling the at least one channel with a polymeric material;
(e) curing the polymeric material to provide a microsensor; and
(f) removing the microsensor from the mold.

44. The method of claim 43, wherein
providing the mold comprises providing a mold wherein the at least one channel comprises at least three sections: a first channel section adjacent to a side edge of the mold; a second channel section adjacent to the first channel section; and a third channel section adjacent to the second channel section; and
wherein the first channel section has a first channel width, wherein the third channel section has a third channel width that is smaller than the first channel width, and wherein the second channel section has channel walls that taper from an end of the first channel section to an end of the third channel section; and
placing the support material in the at least one channel in the mold comprises placing the support material such that the support material is present in the first channel section and wherein a length of the electron conducting fiber is present the second and third section of the channel.

45. The method of claim 44, further comprising sealing an end of the microsensor adjacent to the first channel section with a resin.

46. The method of claim 45, wherein the resin is an epoxy resin.

47. The method of claim 44, wherein the first channel section has a length of about 15 millimeters (mm) or longer.

48. The method of claim 44, wherein the second channel section has a length of about 5 mm or longer.

49. The method of claim 44, wherein the third channel section has a length of about 3 mm or longer.

50. The method of claim 44, wherein the first channel width ranges from about 200 µm to about 1000 µm.

51. The method of claim 50, wherein the first channel width is about 640 µm.

52. The method of claim 44, wherein the third channel width ranges from about 10 µm to about 200 µm.

53. The method of claim 52, wherein the third channel width is about 150 µm.

54. The method of claim 43, further comprising trimming exposed fiber to a desired length.

55. The method of claim 43, wherein the curing is performed by heating the mold to a first temperature for a first period of time.

56. The method of claim 55, wherein the first temperature is between about 100° C. and about 150° C. and/or wherein the first period of time is between about 5 minutes and about 60 minutes.

57. The method of claim 56, wherein the first temperature is about 150° C. and/or wherein the first period of time is about 30 minutes.

58. The method of claim 43, further comprising adding additional polymeric material to the channel following the curing and then curing the additional polymeric material.

59. The method of claim 43, wherein the mold comprises a plurality of channels and the method comprises preparing a plurality of microsensors by preparing a microsensor in each of the plurality of the channels simultaneously.

60. The method of claim 43, wherein the mold is reused one or more times to make one or more additional microsensors.

61. A microsensor prepared according to the method of claim 43.

62. The method of claim 43, wherein the support material comprises a glass capillary material or a metal material.

63. The method of claim 43, wherein another length of the electron conducting fiber is positioned outside the channel or in a channel section having a width such that when the fiber is present in the channel section the fit is secure enough to retard polymeric material from flowing into the channel section.

64. A microsensor array comprising at least two microsensors of claim 1.

* * * * *